United States Patent
Knopov et al.

(10) Patent No.: US 8,956,572 B2
(45) Date of Patent: Feb. 17, 2015

(54) SINGLE USE SYSTEM FOR STERILELY PRODUCING LIPID-NUCLEIC ACID PARTICLES

(71) Applicant: Nitto Denko Corporation, Osaka (JP)

(72) Inventors: Victor Knopov, Oceanside, CA (US); Richard P. Witte, San Diego, CA (US); Priya Karmali, San Diego, CA (US); Robin Lee, San Diego, CA (US); David Webb, Oceanside, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 13/669,217

(22) Filed: Nov. 5, 2012

(65) Prior Publication Data

US 2013/0164400 A1 Jun. 27, 2013

Related U.S. Application Data

(63) Continuation of application No. PCT/IB2012/002916, filed on Nov. 2, 2012.

(60) Provisional application No. 61/556,124, filed on Nov. 4, 2011.

(51) Int. Cl.

| | | |
|---|---|---|
| *B01J 19/00* | (2006.01) | |
| *A61K 9/48* | (2006.01) | |
| *A61K 9/127* | (2006.01) | |
| *B01J 13/00* | (2006.01) | |
| *C12N 15/11* | (2006.01) | |
| *B01J 13/04* | (2006.01) | |
| *B01J 13/12* | (2006.01) | |

(Continued)

(52) U.S. Cl.
CPC .............. *A61K 9/4833* (2013.01); *A61K 9/1271* (2013.01); *A61K 9/1272* (2013.01); *A61K 9/1277* (2013.01); *B01J 13/00* (2013.01); *C12N 15/111* (2013.01); *C12N 2310/11* (2013.01); *C12N 2310/14* (2013.01); *C12N 2320/32* (2013.01); *B01J 13/04* (2013.01); *B01J 13/12* (2013.01); *A61K 48/00* (2013.01); *A61K 47/48815* (2013.01)
USPC ............................................ 422/130; 422/129

(58) Field of Classification Search
USPC .......... 422/128, 130, 131, 132, 129; 436/164, 436/180
See application file for complete search history.

(56) References Cited

U.S. PATENT DOCUMENTS 4,781,871 A * 11/1988 West et al. ...................... 264/4.3
4,895,452 A 1/1990 Yiournas et al.

(Continued)

FOREIGN PATENT DOCUMENTS

| WO | WO 01/05373 | 1/2001 |
|---|---|---|
| WO | WO 2005/090403 | 9/2005 |

(Continued)

OTHER PUBLICATIONS

U.S. Appl. No. 13/669,078, filed Nov. 5, 2012, Knopov.

(Continued)

*Primary Examiner* — Jill Warden
*Assistant Examiner* — Dwayne K Handy
(74) *Attorney, Agent, or Firm* — Baker & Hostetler LLP

(57) ABSTRACT

What is described is a process of forming lipid-nucleic acid nanoparticles simply and reproducibly under aseptic conditions comprising single use components.

22 Claims, 2 Drawing Sheets

(51) Int. Cl.
*A61K 48/00* (2006.01)
*A61K 47/48* (2006.01)

(56) References Cited

U.S. PATENT DOCUMENTS

| | | | |
|---|---|---|---|
| 5,653,996 A * | 8/1997 | Hsu | 424/450 |
| 5,976,567 A | 11/1999 | Wheeler et al. | |
| 5,981,501 A | 11/1999 | Wheeler et al. | |
| 6,395,302 B1 | 5/2002 | Hennink et al. | |
| 6,712,963 B2 | 3/2004 | Schick | |
| 6,843,942 B2 | 1/2005 | Katinger et al. | |
| 6,855,277 B2 | 2/2005 | Baker et al. | |
| 6,855,296 B1 | 2/2005 | Baker et al. | |
| 6,858,225 B2 | 2/2005 | Semple et al. | |
| 7,052,603 B2 | 5/2006 | Schick | |
| 7,094,423 B1 | 8/2006 | Maurer et al. | |
| 7,223,887 B2 | 5/2007 | Gaucheron et al. | |
| 7,410,587 B2 | 8/2008 | Schick | |
| 7,468,151 B2 | 12/2008 | van Buitenen et al. | |
| 7,629,167 B2 | 12/2009 | Hodge et al. | |
| 7,901,708 B2 | 3/2011 | MacLachlan et al. | |
| 2003/0129221 A1 | 7/2003 | Semple et al. | |
| 2004/0142025 A1 | 7/2004 | MacLachlan et al. | |
| 2005/0196435 A1 | 9/2005 | Baker et al. | |
| 2009/0191259 A1 | 7/2009 | Li et al. | |
| 2009/0277833 A1 | 11/2009 | Mir et al. | |
| 2010/0025872 A1 | 2/2010 | Hashiba | |
| 2010/0041152 A1 | 2/2010 | Wheeler et al. | |
| 2010/0112042 A1 | 5/2010 | Polisky et al. | |
| 2010/0316696 A1 | 12/2010 | Wiggenhorn et al. | |
| 2011/0024929 A1 | 2/2011 | Nakamura et al. | |
| 2011/0117125 A1 | 5/2011 | Hope et al. | |
| 2011/0177130 A1 | 7/2011 | Maurer et al. | |

FOREIGN PATENT DOCUMENTS

| | | |
|---|---|---|
| WO | WO 2007/012191 | 2/2007 |
| WO | WO 2007/051303 | 5/2007 |
| WO | WO 2010/021865 | 2/2010 |
| WO | WO 2011/127255 | 10/2011 |
| WO | WO 2012/170952 | 12/2012 |

OTHER PUBLICATIONS

Batzri et al., "Single bilayer liposomes prepared without sonication," Biochim. Biophys. Acta, Apr. 1973, 298(4), 1015-1019.

Hirota et al., "Simple mixing device to reproducibly prepare cationic lipid-DNA complexes (lipoplexes)," BioTechniques, Aug. 1999, 27(2), 286-290.

International Patent Application No. PCT/US2012/063457: International Search Report and Written Opinion dated Feb. 21, 2013, 15 pages.

Maurer et al., "Spontaneous Entrapment of Polynucleotides upon Electrostatic Interaction with Ethanol-Destabilized Cationic Liposomes," Biophysical J., May 2001, 80(5), 2310-2326.

Yadava et al., "Effect of Lyophilization and Freeze-thawing on the Stability of siRNA-liposome Complexes," AAPS PharmSciTech, Jun. 2008, 9(2), 335-341.

Wagner et al., "Liposomes Produced in a Pilot Scale: Production, Purification and Efficiency Aspects", European Journal of Pharmaceuticals and Biopharmaceuticals, 2002, 54, 213-219.

International Patent Application No. PCT/IB2012/002916: International Search Report and Written Opinion dated Jul. 17, 2012, 14 pages.

* cited by examiner

Legend

1. Single use mixing bag for lipid dissolution
2. Air vent
3. Temperature Probe
4. Peristaltic pump with single use tubing
5. Single use 0.45/0.2 filter capsule
6. Scale
7. Single use mixing bag for filtered lipids
8. Single use mixing bag for siRNA dissolution
9. Single use mixing bag for siRNA/lipid particle formation
10. 3D single use bag
11. Single use bottle for TFF
12. Metering pump with disposable pump head
13. Pressure gauge
14. Disposable TFF cartridge
15. Single use bottle for bulk product

*Fig. 1B*

SINGLE USE SYSTEM FOR STERILELY PRODUCING LIPID-NUCLEIC ACID PARTICLES

CROSS REFERENCE TO RELATED APPLICATIONS

This application is a continuation of PCT Application No. PCT/IB2012/002916 filed Nov. 2, 2012 and claims the benefit of U.S. Provisional Application No. 61/556,124 filed Nov. 4, 2011. Each of which is hereby incorporated by reference in its entirety.

TECHNICAL FIELD

The description is directed a system for a process of forming lipid-nucleic acid nanoparticles simply and reproducibly under aseptic conditions comprising single use components.

BACKGROUND

Lipids are potentially useful as carriers for delivery of therapeutic molecules, particularly for delivery of nucleic acids. Lipids form liposomes, which can encapsulate, complex, or entrap nucleic acid molecules and thereby enhance delivery of this class of therapeutic molecules to target cells upon administration, e.g., intravenously to the circulation. Their usefulness in pharmaceutical compositions is limited by available methods to produce lipid-nucleic acid nanoparticles reproducibly. Various methods have been devised to produce such nanoparticles.

One method to produce nanoparticles consisting solely of lipids (vesicles) simply and reproducibly without sonication utilizes the ethanol injection described by Batzri et al., 1973, Biophys Biochem Acta 298:1015-19, and Kremer et al., 1977, Biochemistry 16:3932-35, whereby lipids solubilized in ethanol are injected into an aqueous solution to spontaneously form liposomes.

Van Buitenen et al. U.S. Pat. No. 7,468,151 describe a closed circuit system for sterilizing microparticles, including liposomes. The circuit system includes of a mixing chamber connected to a transflow filtration (TFF) unit. The TFF unit purifies a liquid dispersion of microparticles under aseptic conditions. The liquid is pumped aseptically from the mixing chamber through the TFF. The material retained in the TFF (the retentate) is recycled through the mixing chamber and the TFF unit until purified. The purification process is performed aseptically in one apparatus without removing the microparticles in the TFF retentate.

Others describe the process of producing nucleic acid-liposome particles by using specific methods to combine lipids and nucleic acids. Hirota et al., 1999, BioTechniques 27:286-89, teaches that liposomes coated with nucleic acids molecules spontaneously form when cationic lipids in ethanol are injected into an aqueous solution of nucleic acid. Maurer et al., 2001, Biophysical J, 80:2310-26 and Maurer et al. U.S. Pat. No. 7,094,423 teach a method of encapsulating nucleic acid molecules in a liposome. This method involves use of a preformed liposome comprising a cationic lipid. The liposome is destabilized by adding ethanol to the aqueous solution. Nucleic acid molecules are added to the destabilized lipid. Upon removal of ethanol, the liposome encapsulates the nucleic acid while reforming. An alternative method to encapsulate nucleic acids in liposomes is taught by Semple et al., 2001, Biophys Biochem Acta 1510:152-66 and Semple et al. U.S. Pat. No. 6,858,225. This method increases encapsulation efficiency by using an ionizable cationic lipid to form liposomes. An ethanol solution of lipids is combined with nucleic acids in an aqueous solution buffered at low pH. Ethanol is then removed while raising the pH to neutral value. Both methods require further processing of the resulting liposomes because aggregation during reconstitution produces a wide variation in size.

MacLachlan et al. U.S. Pat. No. 7,901,708 describes a process and an apparatus for producing uniform sized liposomes that encapsulate a nucleic acid. A stream RNA in an aqueous buffer is mixed with a stream of cationic lipids in ethanol at approximately equal flow rates in a T connector, in which lipid vesicles form instantly in a high ethanol concentration (45%). The solvent and solute concentrations are kept constant throughout the mixing process. No static mixers are involved. in which the liposomes are diluted. The stable nucleic acid liposomes are sterilized at the end of the process, immediately before a sterile fill step.

The methods described above require extensive labor to minimize bacterial contamination during the process of producing liposomes, including autoclaving, washing, and satisfying regulatory burdens. There remains an unmet need for a manufacturing method to encapsulate nucleic acids without the need for extensive mechanical processing steps to prepare preformed liposomes and without the need for processing step to reduce lipid-nucleic acid particles to a monodisperse population.

SUMMARY

One aspect of the description is a system for sterilely preparing a lipid-nucleic acid nanoparticle, comprising:

a $1^{st}$ holding unit for an organic lipid solution comprising lipids in a water-miscible organic solvent;

a $2^{nd}$ holding unit for an aqueous solution comprising a therapeutic drug;

a mixing unit with a static mixer, an injection means to add the organic lipid solution to the mixing chamber;

a $3^{rd}$ holding unit for an aqueous buffer;

a dilution unit;

a concentrating unit comprising a transflow filter for concentrating the liposome suspension and removing the organic solvent; and a single use bed for collecting the concentrated liposome suspension after removal of organic solvent;

wherein the mixing unit contains the aqueous drug solution, and the lipid solution is steadily added to the drug solution in the mixing unit for at least 5 minutes to produce a lipid-drug mixture having a lipid:RNA ratio of at most 12:1, wherein the lipid-drug mixture is transferred to the dilution unit and is diluted by addition of the aqueous buffer;

and wherein the system consists of components that are sterilized and disposable so as to be adapted for single batch usage. The system may further comprise a unit for preparing the organic lipid solution connected to the $1^{st}$ holding unit. The system may further comprise a filter for sterilizing the organic lipid solution while said solution is being transferred to the $1^{st}$ holding unit. The system may further comprise a lipid solution, drug solution, lipid-drug mixture, and suspension that are sterile. The concentrating unit may comprises a diaphragm metering pump with a single use pump chamber. The lipids may comprise a cationic lipid, a helper lipid, a sterol, and a polyethylene (PEG)-lipid conjugate, and further comprise a targeting lipid. The therapeutic drug is a dsRNA molecule. The concentration of lipid and dsRNA in the mixture consists of a lipid:RNA charge ratio of 2.5. The water-miscible organic solvent may be ethanol. The $1^{st}$ and $2^{nd}$ solutions may be combined at a temperature of 35 to 40° C. The 2$^{nd}$ holding unit may contain a therapeutic drug in an aqueous buffer at pH 3.5 to pH 4.5. The 3$^{rd}$ holding unit may contain an aqueous buffer at neutral pH. The mean particle diameter of the liposome encapsulating the therapeutic drug may be 80 nm to 150 nm. The injection means comprises an injection port that delivers the organic solution to the air water interface of the aqueous solution in the mixing unit, or alternately an injection port that is submerged in the aqueous solution in the mixing unit and delivers the organic solution thereto. The system may further comprises a lyophilization step. The lyophilization step may comprise a freezing step and a drying step. The aqueous buffer may comprise sucrose or trehalose. The freezing step may cool the lipid-drug mixture at 1° C./minute from 20 to −40° C. The drying step comprises a step of drying the lipid-drug mixture at about −15 to about −35° C.

BRIEF DESCRIPTION OF THE DRAWINGS

FIG. 1B provides a legend for FIG. 1A.

DETAILED DESCRIPTION OF ILLUSTRATIVE EMBODIMENTS

Figure 1A:
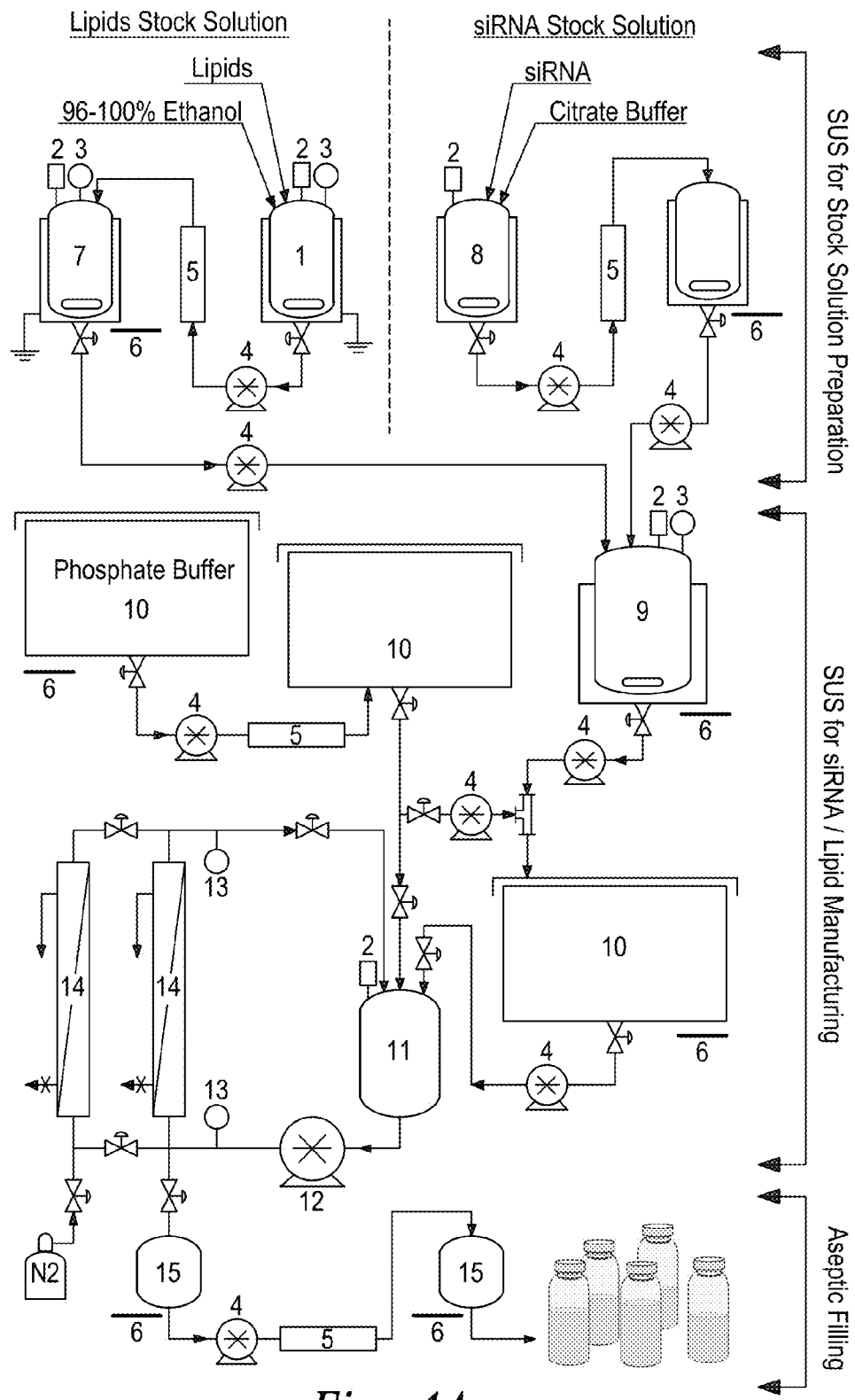
FIG. 1A shows a single-use system of the description.

The description herein provided relates a method for making lipid-encapsulated therapeutic molecules, including negatively-charged therapeutic polymers, e.g., nucleic acids, proteins, and peptides. The description herein provided includes a method for making lipid-encapsulated nucleic acid molecules. The method is particularly amenable to large-scale manufacture of particles consisting of liposome-encapsulated therapeutic molecules. The method provides the unexpected and surprising result that the particles produced are monodisperse (i.e. less than 0.2 polydispersity index (PDI), as defined herein), a narrow and uniform size distribution between 50 and 150 nm. This method provides a means of encapsulating by combining lipids solubilized in a water-miscible organic solvent, such as ethanol, with negatively-charged therapeutic polymers solubilized in an aqueous solution, and removing the organic solvent. The absolute and relative concentrations of the lipids and negatively-charged therapeutic polymers are sufficient to produce small particles. The particles produced by the method of the description do not require mechanical processing, such as extrusion, to obtain a monodisperse population.

The method of the description has the advantage over previous methods by the ease in which can be scaled up to large volumes and that it is robust over a wide range of temperatures, solutes, pH, and processing times.

The method of the description has the advantage over previous methods by reproducibly producing a uniform population of particles without extra steps required to produce preformed vesicles.

The method of the description has the advantage over previous methods by reproducibly producing a uniform population of nanoparticles without extra steps required to mechanically process particles produced upon mixture of lipids and negatively charged therapeutic polymers. These extra steps include, for example sonication, homogenization, or extrusion, to reduce their size and achieve uniformity to a therapeutically acceptable range.

The method of the description has the advantage of achieving nucleic acid encapsulation efficiency equal to or better than previous methods without extra processing steps to produce nanoparticles.

Other advantages of the method of the description will become apparent as further detail is provided in the description herein regarding lipid components and conditions.

The following abbreviations are used in the description.
VF: vent filter
TG: temperature gauge
SUB: single use bed
TFF: transflow filter
PP: peristaltic pump
PG: pressure gauge
Scale: a means of measuring weight FIGS. 1A and 1B show a single-use system comprising the following elements.

Lipid Stock: this vessel contains selected lipids in an organic, water-miscible solvent. Ethanol is shown as the preferred solvent. The concentration of lipids may be adjusted to increase throughput. The vessel consists of a disposable bag with a TG and a mixing means. The bag has openings for adding lipids in 96-100% ethanol, a VF, and an exit tube, which is controlled by a valve. The bag is housed in a heatable, reusable, electrically grounded container. The bag has a means for adding additional ethanol to dilute the lipid solution to an operating concentration.

PP1: peristaltic pump 1. This pumps lipid stock from the Lipid Stock vessel through a 0.45/0.22 μm Filter to the Filtered Lipid Stock vessel.

Filtered Lipid Stock: this vessel contains lipids at the operating concentration. The vessel is a disposable bag with a mixing means and a TG. It has openings for entry of lipid stock, a VF and an exit tube, which is controlled by a valve. The bag is housed in a heatable, reusable, electrically grounded container with a Scale.

sRNA Stock: this vessel contains selected a drug in an aqueous buffer. siRNA is the preferred drug, and citrate buffer is the preferred buffer. The concentration may be adjusted to increase throughput. The vessel is a disposable bag with a mixing means. The bag has openings for adding solute and solvent, and an exit tube, which is controlled by a valve. The bag has a means for adding additional buffer to dilute the RNA solution to an operating concentration.

PP2: peristaltic pump 2. This pumps siRNA stock from the siRNA Stock vessel through a 0.45/0.22 μm Filter to the Filtered siRNA Stock vessel.

Filtered siRNA Stock: this vessel contains siRNA at operating concentration. This element contains a scale. The vessel is a disposable bag housed in a reusable container. It has an opening(s) for siRNA stock and an exit tube, which is controlled by a valve. The bag is housed in a reusable container with a Scale.

PP3: peristaltic pump 3 for transferring filtered lipid stock to the vessel labelled Liposomal siRNA in 35% Ethanol. It is equipped with a PG (PG1).

PP4: peristaltic pump 4 for transferring filter siRNA stock to the Liposomal siRNA in 35% Ethanol vessel. It is also equipped with a PG (PG2).

Liposomal siRNA in 35% Ethanol: this vessel contains the mixture of liposomes and drug at 35% ethanol. This element contains a VF and a TG. Openings for filtered lipid and siRNA stock are separated from an exit tube, which is controlled by a valve. The preferred unit is a disposable bag housed in a reusable container.

Phosphate Buffer: this vessel contains a buffer (preferably a phosphate buffer), a mixing means, and a Scale. It is a large vessel with an opening lid, and an exit tube with a valve.

Filtered Phosphate Buffer: this vessel is connected to the Phosphate Buffer vessel by tubing, a 0.45/0.22 μm Filter, and a peristaltic pump. It has a mixing means and an exit tube with a valve leading to tubing through PP 5 to the Liposomal siRNA in 10% Ethanol vessel and TFF SUB vessel. The vessel is a reusable container lined with a disposable liner.

PP 5: this pumps filtered phosphate buffer from the Filtered Phosphate Buffer vessel to Liposomal siRNA in 35% Ethanol vessel and to the TFF SUB vessel. PP 5 is coupled to a PG (PG4).

Liposomal siRNA in 10% Ethanol: this vessel contains the mixture of liposomes and drug in 10% ethanol after dilution of liposomes and drug at 35% ethanol by the buffer in the Filtered Phosphate Buffer vessel. The vessel is a reusable container lined with a disposable liner, with an inlet for liposomal siRNA solution, a VF, a Scale, and an exit port with a valve leading to the TFF SUB vessel.

PP 6: this pumps liposomes and drug in 10% ethanol from Liposomal siRNA in 10% Ethanol vessel the through a 0.45/0.22 µm Filter to the TFF SUB vessel.

TFF SUB: this vessel contains entry ports for liposomes and drug in 10% ethanol from the Liposomal siRNA in 10% Ethanol vessel, for buffer from the Filtered Phosphate Buffer vessel, and for retentate from the TFF unit, each with a valve. It also contains a VF and an exit port with its valve.

Metering Pump with Disposable Pump Head: this high pressure pump coupled with two PGs (PG 3 and PG 4). It transfers liposome and drug from TFF SUB to the TFF unit.

TFF: this unit is identified as pair of rectangles with a diagonal line. During operation the liposome/drug in ethanol solution passes through the TFF unit to remove ethanol. The ethanol removed by the TFF unit exits the system. More than a single TFF can be operated in parallel, connected by valves. The retained solution (retentate) exits the TFF, recirculates to the TFF SUB, and recycles through the TFF unit as needed to remove all of the ethanol. A pressure gauge (PG 4) monitors pressure of the retentate. Nitrogen gas stored in a tank $N_2$ is used to augment the metering pump, as needed to create backpressure, and eventually facilitate transfer of TFF retentate to a first 10 L SUB vessel.

10 L SUB: this is a single use vessel equipped with a scale. Optionally, the SUS include a series of three 10 L SUB vessels. The TFF retentate is pumped through a 0.45/0.22 µm Filter to reduce the bioburden and to ensure that the product is completely free from microbial contamination resulting from microbial contamination that may have entered the processing stream. If the full process train is truly aseptic, then it may be possible to omit the latter filtration steps. The resulting TFF retentate is packaged during Aseptic Filling.

Aseptic Filling: This step precedes lyophilization, which is performed as a separate process using different equipment. The aseptic filling step prior to lyophilization may include addition of carrier material, such as mannose, glucose, or other materials for providing bulk, or for stabilizing RNA during the lyophilization step.

The system is arranged for manual control of movement of materials through each step. All components in contact with the lipids, drug, solvents, and buffers are single use and are disposable. The system is shown for a 10 L batch, and is scalable up to more than 1000 L. Components are designed to be used once per batch of liposome/drug.

The means to accomplish the process of manufacture lays in a sequence of steps as shown in a flow diagram (FIGS. 1A and 1B) as follows.

Lipid and drug stock solutions are separately prepared in Lipid Stock and siRNA Stock vessels. The stock solutions can be prepared at high concentration. Mixing occurs by stirring in the stock vessels. The temperature of the lipid stock solution can be adjusted to a set temperature. The vessel used for preparing lipid stock is chosen to have minimal leachable material when pure organic solvent is used at an elevated temperature.

The stock solutions are separately pumped through a 0.45/0.22 µm Filter to a Filtered Lipid Stock vessel and Filtered siRNA Stock vessel. The stock solutions may be combined with more solvent to dilute the stock solution before or during transfer to the filtered stock vessels.

In the same way, aqueous buffer is prepared in the Phosphate Buffer vessel, and is filter sterilized by pumping to a Filtered Phosphate Buffer vessel.

The filtered siRNA solution is pumped to the Liposomal siRNA in 35% Ethanol vessel.

Lipid in organic solvent is pumped into the aqueous siRNA solution in the Liposomal siRNA in 35% Ethanol vessel at a rate effective to form lipid-drug particles in a final concentration of 35% ethanol under a controlled set temperature while mixing the aqueous solution.

The addition of lipid may occur via a single port or multiple ports, through a needle or set of needles. It may occur from above to the surface of the aqueous solution, or it may be injected into the aqueous solution from below the surface. Through addition and mixing, the ethanol concentration of the solution in the Liposomal siRNA in 35% Ethanol vessel increases to 30% to 40%, preferably 35%. The increase is gradual, forming a gradient from an initial (preferably 0%) to final (preferably 35%) values. This gradient may extend from 1 minute to 60 minutes or longer.

Once the solution the Liposomal siRNA in 35% Ethanol vessel reaches a final ethanol concentration (preferably 35%), the solution is pumped out of the Liposomal siRNA in 35% Ethanol vessel and mixed in line with buffer separately pumped from the Filtered Phosphate Buffer vessel so as to dilute the mixture in a water miscible alcohol, preferably 10% to 20% ethanol, most preferably 10% ethanol, and transferred to the Liposomal siRNA in 10% Ethanol vessel.

The 10% ethanol solution is diafiltered against the aqueous buffer to remove the ethanol.

The TFF retentate (0% ethanol, 100 aqueous buffer) is stored in the first 10 L SUB.

The TFF retentate may optionally be filtered to reduce the bioburden for Aseptic Filling Aseptic Filling includes a step of lyophilization. The lyophilization step is discontinuous with the process of generating the sterile TFF retentate at step 10. That is, this step preferably is performed at a different location than the SUS unit providing the TFF retentate. A carbohydrate such as sucrose or glucose may possibly be added prior to lyophilizing to stabilize the nanoparticles and/or add bulk.

The lipid mixture used in the method of the description contains at least a positively charged lipid (cationic lipid) to complex with the negatively-charged therapeutic polymers, and a polyethylene glycol-containing lipid conjugate (PEG-lipid) to prevent aggregation. The cationic lipid can be a permanent cationic charge over a wide range of pH conditions, an ionizable cationic lipid, which is charged at low pH (less than pH 6) and without a net charge at neutral pH (pH 6.5 to 8), or a combination of permanent and ionizable cationic lipids. The lipid mixture can also contain a targeting lipid, a polymer, a steroid, a phospholipid, or a member of another lipid group, including a fat, a wax, fat-soluble vitamin, monoglyceride or diglyceride, fatty acyls, glycerolipids, glycerophospholipids, sphingolipids, saccharolipids and polyketides. This method can also be used for the formation of liposomes with only neutral or negatively charged components.

Preferentially the components of the lipid mixture may be selected from the following groups.

Cationic Lipid

Within the scope of the description are cationic lipids of formula I $C_{20}$alkenyl. $C_{12}$-$C_{18}$alkenyl, $C_{13}$-$C_{17}$alkenyl, $C_{17}$alkenyl; $R_3$ and $R_4$ are each independently hydrogen, $C_1$-$C_6$alkyl, or —$CH_2CH_2OH$, $C_1$-$C_6$alkyl, $C_1$-$C_3$alkyl; n is 1-6; and X is a counterion, including any nitrogen counterion, as that term is readily understood in the art. Preferred nitrogen counterions include halogens, with chloride and bromide being particularly preferred. Another preferred counterion is mesylate (—$SO_3CH_3$).

Exemplary compounds of formula I include:

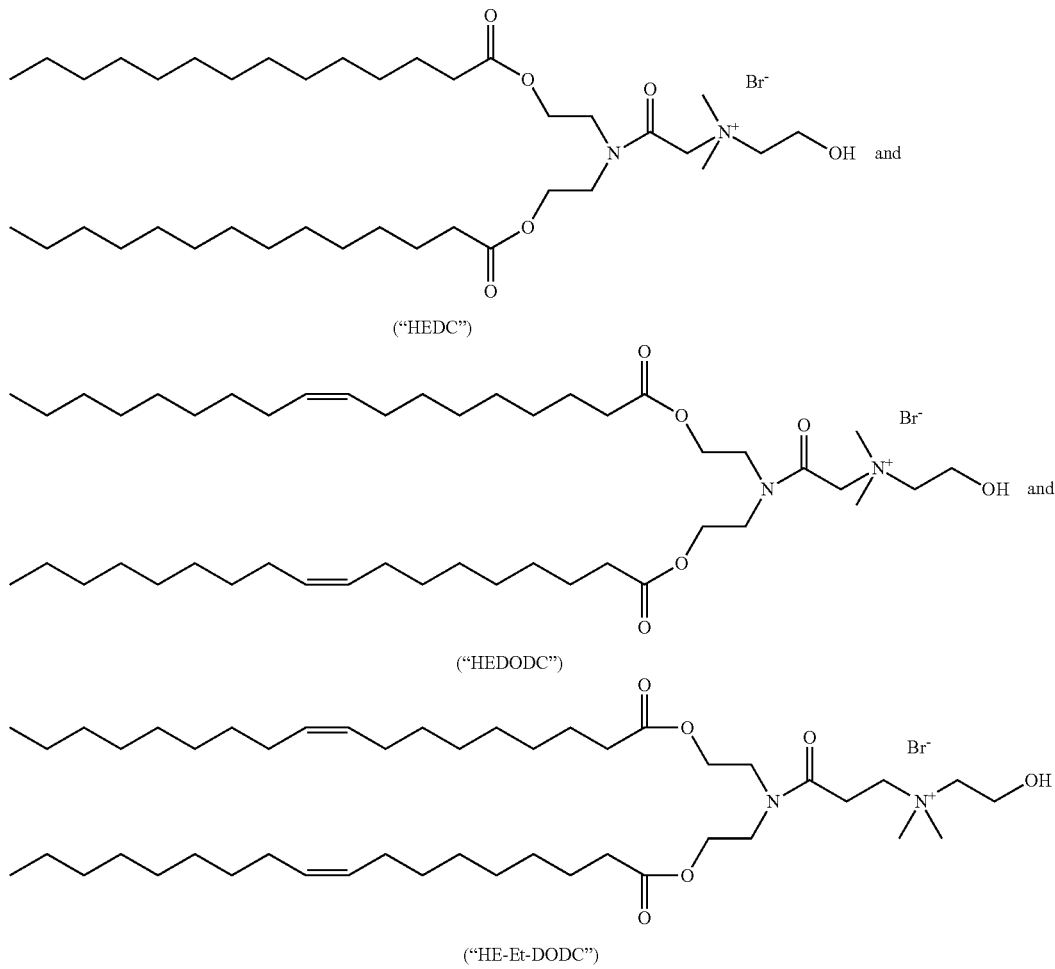

("HEDC")

("HEDODC")

("HE-Et-DODC")

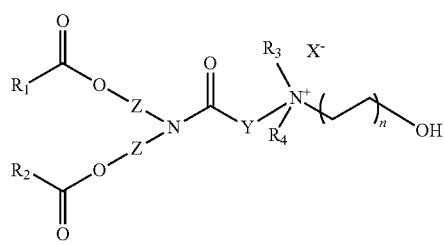

in which
Z=an alkyl linker, $C_2$-$C_4$ alkyl
Y=an alkyl linker, $C_1$-$C_6$ alkyl
$R_1$ and $R_2$ are each independently $C_{10}$-$C_{30}$alkyl, $C_{10}$-$C_{30}$alkenyl, or $C_{10}$-$C_{30}$alkynyl, $C_{10}$-$C_{30}$alkyl, $C_{10}$-$C_{20}$alkyl, $C_{12}$-$C_{18}$alkyl, $C_{13}$-$C_{17}$alkyl, $C_{13}$alkyl, $C_{10}$-$C_{30}$alkenyl, $C_{10}$-

Other cationic charged lipids at physiological pH include, but are not limited to, N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleyloxy)propyl)-N,N,N-trimethylammonium chloride ("DOTAP"); N-(1,2-dimyristyloxyprop-3-yl)-N,N-dimethyl-N-hydroxyethylammonium bromide ("DMRIE"), 3β-(N—(N',N'-dimethylaminoethane)carbamoyl)cholesterol ("DC-Chol"), dioctadecylamidoglycyl carboxyspermidine ("DOGS"); and N-(1-(2,3-dioleyloxy)propyl)-N-(2-(sperminecarboxamido)ethyl)-N,N-dimethylammonium trifluoroacetate ("DOSPA").

Ionizable Cationic Lipids.

Within the scope of the description are ionizable cationic lipids of formula II

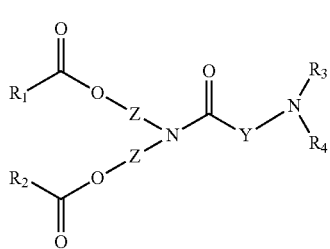

in which
Z=an alkyl linker, $C_2$-$C_4$ alkyl, —$CH_2SCH_2CH_2$
Y=an alkyl linker, $C_1$-$C_6$ alkyl $R_1$ and $R_2$ are each independently $C_{10}$-$C_{30}$alkyl, $C_{10}$-$C_{30}$alkenyl, or $C_{10}$-$C_{30}$alkynyl, $C_{10}$-$C_{30}$alkyl, $C_{10}$-$C_{20}$alkyl, $C_{12}$-$C_{18}$alkyl, $C_{13}$-$C_{17}$alkyl, $C_{13}$alkyl, $C_{10}$-$C_{30}$alkenyl, $C_{10}$-$C_{20}$alkenyl, $C_{12}$-$C_{18}$alkenyl, $C_{13}$-$C_{17}$alkenyl, $C_{17}$alkenyl; $R_3$ and $R_4$ are each independently hydrogen, $C_1$-$C_6$alkyl, or —$CH_2CH_2OH$, $C_1$-$C_6$alkyl, $C_1$-$C_3$alkyl.

Some positively charged lipids have a pKa at or near physiological pH and are cationic in mild acid conditions and weakly cationic at physiological pH. Such ionizable cationic lipids include, but are not limited to, ((2-((2-(dimethylamino)ethyl)thio)acetyl)azanediyl)bis(ethane-2,1-diyl)ditetradecanoate ("S104"), (Z)-((3-(dimethylamino)propanoyl)azanediyl)bis(ethane-2,1-diyl)dioleate ("i-Et-DODC"), N-(2,3-dioleyloxy)propyl)N,N-dimethylammonium chloride ("DODMA") and 1,2-dioleoyl-3-dimethylammonium-propane ("DODAP").

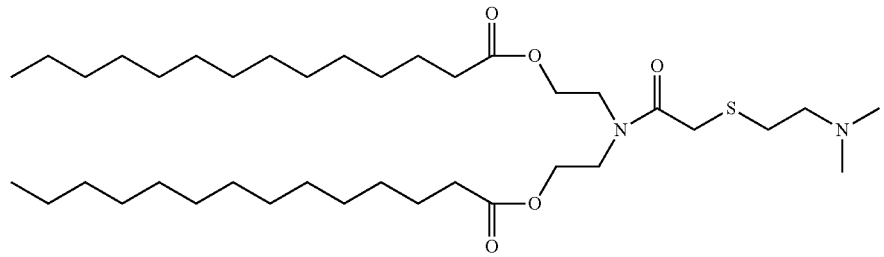

S104

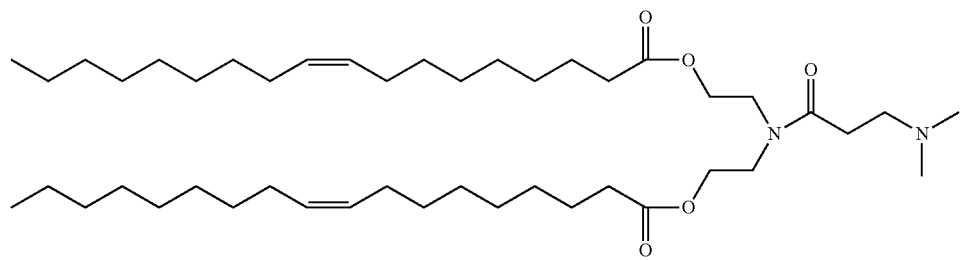

i-Et-DODC

It is recognized that ionizable lipids may facilitate the binding and/or release of the active pharmaceutical ingredient (API), as shown below.

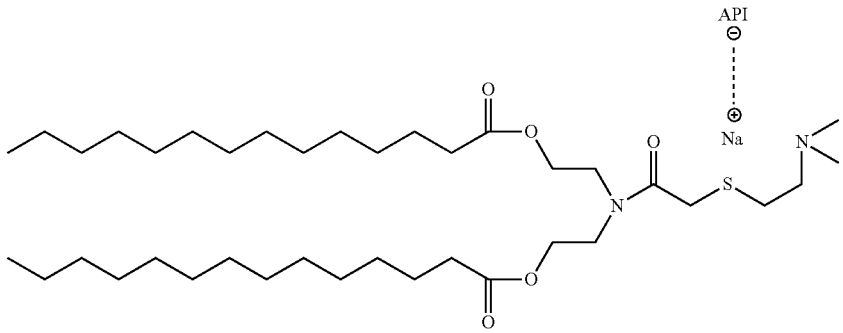 [SMILES: "API" ; CCCCCCCCCCCCCC(=O)OCCN(CCOC(=O)CCCCCCCCCCCCC)C(=O)CSCCN(C)C ; [Na+]]

Neutral Lipids

Examples of neutral lipids include, but are not limited to, phospholipids, aminolipids and sphingolipids. Neutral lipids include amphipathic lipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine ordilinoleoylphosphatidylcholine. Other compounds lacking in phosphorus, such as sphingolipid, glycosphingolipid families, diacylglycerols and 3-acyloxyacids, are also within the group designated as amphipathic lipids. Additionally, the amphipathic lipid described above can be mixed with other lipids including triglycerides and sterols.

PEG-Lipids

A bilayer stabilizing component is polyethyleneglycol ("PEG") conjugated to a lipid head group, e.g., phosphatidylethanolamine. Another bilayer stabilizing component is PEG conjugated to a ceramide. PEG can be conjugated to a phosphatidylethanolamine or, alternatively, to a ceramide using standard coupling reactions known to and used by those of skill in the art. In addition, preformed PEG-phosphatidylethanolamine ("PEG-PE") conjugates are commercially available.

PEGs of varying molecular weights can be used to form the bilayer stabilizing components of the present invention. PEGs of varying molecular weights are commercially available from a number of different sources or, alternatively, they can be synthesized using standard polymerization techniques well-known to those of skill in the art. In a presently preferred embodiment, the polyethylene glycol has a molecular weight ranging from 200 to 10000 Da, preferably 500 to 4000 Da, and most preferably 1000 to 2000 Da. Generally, it has been found that increasing the molecular weight of the PEG reduces the concentration of the bilayer stabilizing component required to achieve stabilization.

Phosphatidylethanolamine having a variety of acyl chain groups of varying chain lengths and degrees of saturation can be conjugated to PEG to form the bilayer stabilizing component. Such phosphatidylethanolamines are commercially available, or can be isolated or synthesized using conventional techniques known to those of skill in the art. Phosphatidylethanolamines containing saturated or unsaturated fatty acids with carbon chain lengths in the range of C10 to C20 are preferred. Phosphatidylethanolamines with mono- or diunsaturated fatty acids and mixtures of saturated and unsaturated fatty acids can also be used. Suitable phosphatidylethanolamines include, but are not limited to, the following: dimyristoylphosphatidylethanolamine (DMPE), dipalmitoylphosphatidylethanolamine (DPPE), dioleoylphosphatidylethanolamine (DOPE) and distearoylphosphatidyl-ethanolamine (DSPE).

The forgoing compositions can also include PEG-conjugated lipids, which are known in the art per se, including PEG-phospholipids and PEG-ceramides, including one or more molecules selected from the following: PEG2000-DSPE, PEG2000-DPPE, PEG2000-DMPE, PEG2000-DOPE, PEG1000-DSPE, PEG1000-DPPE, PEG1000-DMPE, PEG1000-DOPE, PEG550-DSPE, PEG550-DPPE, PEG-550DMPE, PEG-1000DOPE, PEG-cholesterol, PEG2000-ceramide, PEG1000-ceramide, PEG750-ceramide, and PEG550-ceramide.

Furthermore, compositions can also include monodisperse (md) peg-lipids, with general formula mdPEG-linker-lipid, with examples including, but not limited to, 83-hydroxy-3,6,9,12,15,18,21,24,27,30,33,36,39,42,45,48,51,54,57,60,63,66,69,72,75,78,81-heptacosaoxatrioctacontyl (2,3-bis(tetradecyloxy)propyl)carbamate ("HO-PEG1251-cBTP") and 134-hydroxy-3,6,9,12,15,18,21,24,27,30,33,36,39,42,45,48,51,54,57,60,63,66,69,72,75,78,81,84,87,90,93,96,99,102,105,108,111,114,117,120,123,126,129,132-tetratetracontaoxatetratriacontahectyl (2,3-bis(tetradecyloxy)propyl)carbamate ("HO-PEG2000-cBTP") as examples.

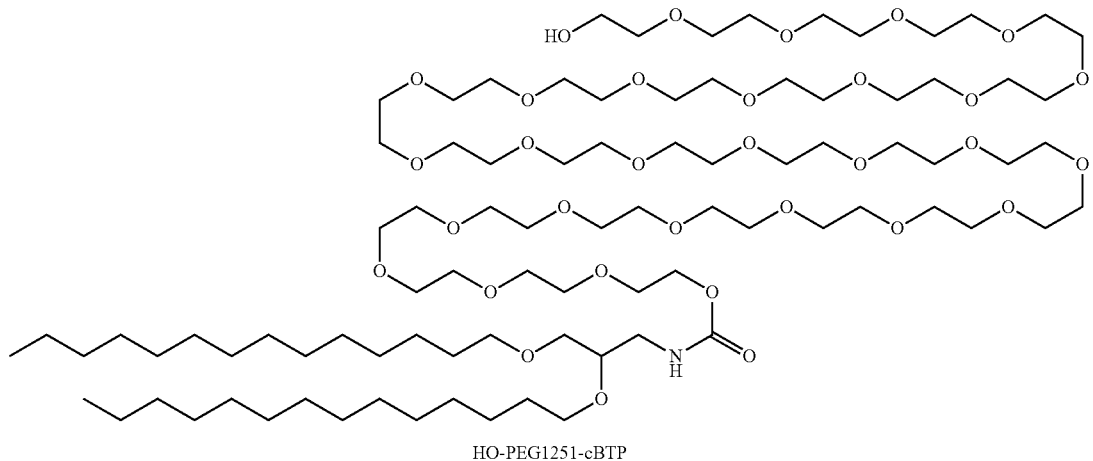

HO-PEG1251-cBTP

-continued

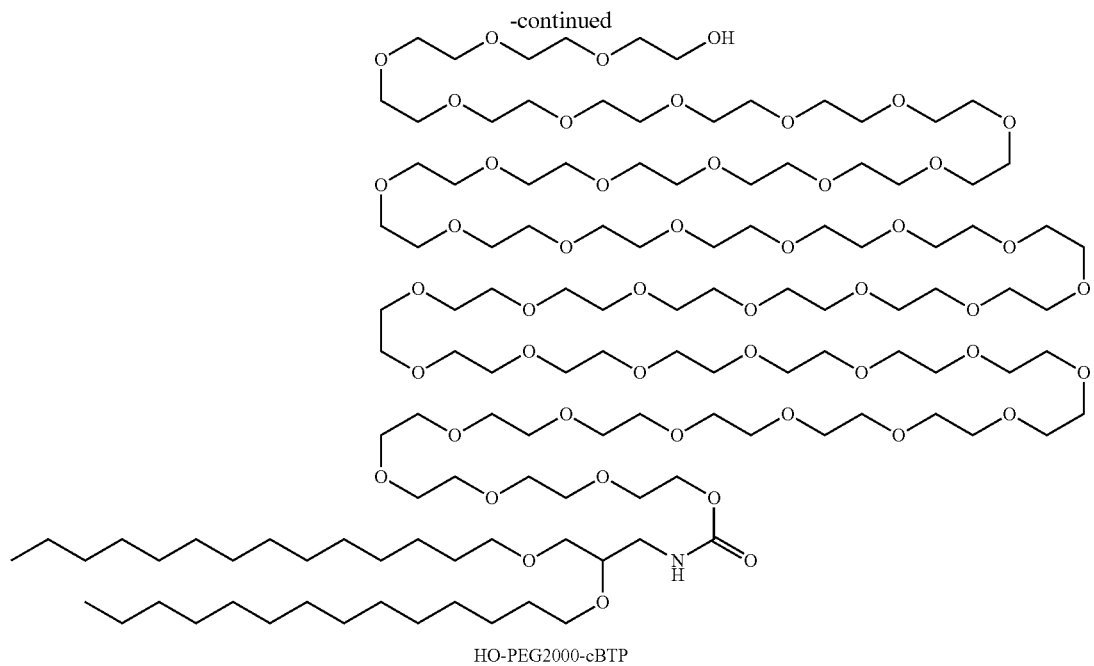

HO-PEG2000-cBTP

Steroids

Steroids include cholestanes (e.g., cholesterol), cholanes and bile acids (e.g., chenodeoxycholate and cholate), ergosterol, lanosterol, corticosteroids (e.g., glucocorticoid), pregnane (e.g., progesterone), and phytosterols. These can be included also in the form of a conjugate with a hydrophilic moiety, e.g., a polyethylene glycol. A preferred steroid is cholesterol.

Targeting Lipid

An example of a targeting lipid is a compound of the formula (A),

L-X—R     A in which lipid (L) is selected from the group consisting of DSPE, DOPE, and DC; linker (X) is selected from the group consisting of nothing, PEG550, PEG2000, PEG-glutamate (-Glu), Glu, C6, glycine, and GluNH, N1,N19-bis(3-(2-(2-(3-aminopropoxy)ethoxy)ethoxy)propyl)-4,7,10,13,16-pentaoxanonadecane-1,19-diamide; and retinoid (R) is selected from the group consisting of tretinoin, adapalene, retinol, 4-hydroxy(phenyl)retinamide (4-HPR), retinoic acid (vitamin A), 9-(2,6,6-trimethylcyclohex-1-en-1-yl)nonanoic acid, 3,7-dimethyl-9-(2,6,6-trimethylcyclohex-1-en-1-yl) nonanoic acid, 3,7-dimethyl-9-(2,2,6-trimethylcyclohexyl) nonanoic acid, and any partially or fully saturated retinoid or a derivative thereof.

Another example of a targeting lipid is a compound of the formula (B),

R—X—R     B, in which linker (X) is N1,N19-bis(3-(2-(2-(3-aminopropoxy) ethoxy)ethoxy)propyl)-4,7,10,13,16-pentaoxanonadecane-1,19-diamide ("bisamido-PEG") or N1,N19-bis(16,20-diamino-15-oxo-4,7,10-trioxa-14-azaicosyl)-4,7,10,13,16-pentaoxanonadecane-1,19-diamide ("lys-bisamido-PEG-lys"); and retinoid (R) is selected from the group consisting of tretinoin, adapalene, retinol, 4-hydroxy(phenyl)retinamide (4-HPR), and retinoic acid (vitamin A), 9-(2,6,6-trimethylcyclohex-1-en-1-yl)nonanoic acid, 3,7-dimethyl-9-(2,6,6-trimethylcyclohex-1-en-1-yl)nonanoic acid, 3,7-dimethyl-9-(2,2,6-trimethylcyclohexyl)nonanoic acid, and any partially or fully saturated retinoid or a derivative thereof.

Other targeting molecules can be included in the lipid mixture, e.g., folic acid, vitamin E, peptide ligands and/or monoclonal antibodies.

RNA-Lipid Particle Compositions and Formulations

The description includes compositions comprising a lipid particle with and without an active agent, in which the active agent when present is associated with the lipid particle. In particular embodiments, the active agent is a therapeutic agent. In particular embodiments, the active agent is encapsulated within an aqueous interior of the lipid particle. In other embodiments, the active agent is present within one or more lipid layers of the lipid particle. In other embodiments, the active agent is bound to the exterior or interior lipid surface of a lipid particle.

In certain embodiments, lipid particles of the present invention are associated with a nucleic acid, resulting in a nucleic acid-lipid particle. In particular embodiments, the nucleic acid is fully encapsulated in the lipid particle. As used herein, the term "nucleic acid" is meant to include any oligonucleotide or polynucleotide. Fragments containing up to 50 nucleotides are generally termed oligonucleotides, and longer fragments are called polynucleotides. In particular embodiments, oligonucleotides of the present invention are 15-50 nucleotides in length.

The terms "polynucleotide" and "oligonucleotide" herein refer to a polymer or oligomer of nucleotide or nucleoside monomers consisting of naturally occurring bases, sugars and inter-sugar (backbone) linkages. The terms "polynucleotide" and "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

Oligonucleotides may be as oligodeoxyribonucleotides or oligoribonucleotides. An oligodeoxyribonucleotide consists of a deoxyribose joined covalently to phosphate at the 5' and 3' carbons of this sugar to form an alternating, unbranched polymer. An oligoribonucleotide consists of a similar repeating structure where each nucleotide has a ribose sugar group. Modified ribose molecules may be included in an oligoribonucleotide.

The nucleic acid that is present in a lipid-nucleic acid particle according to this invention includes any form of nucleic acid that is known. The nucleic acids used herein can be single-stranded DNA or RNA, or double-stranded DNA or RNA, or DNA-RNA hybrids or RNA-PNA and/or DNA-PNA hybrids of PNA duplexes. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include, e.g., antisense oligonucleotides, ribozymes, microRNA, and triplex-forming oligonucleotides.

Nucleic acids may be of various lengths, generally dependent upon the particular form of nucleic acid. For example, in particular embodiments, plasmids or genes may be from about 1,000 to 100,000 nucleotide residues in length. In particular embodiments, oligonucleotides may range from about 10 to 100 nucleotides in length. In various related embodiments, oligonucleotides, whether single-stranded, double-stranded, and triple-stranded, may range in length from about 10 to about 50 nucleotides, from about 21 to about 50 nucleotides, from about 15 to about 30 nucleotides, from about 20 to about 30 nucleotides in length.

In particular embodiments, an oligonucleotide (or a strand thereof) may specifically hybridize to or is complementary to a target polynucleotide. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility or expression therefrom, and there is a sufficient degree of specific base-pairing to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, in other embodiments, this oligonucleotide includes 1, 2, or 3 base substitutions as compared to the region of a gene or mRNA sequence that it is targeting or to which it specifically hybridizes.

In particular embodiments, nucleic acid-lipid particles may be associated with RNA interference (RNAi) molecules. RNA interference methods using RNAi molecules may be used to disrupt the expression of a gene or polynucleotide of interest. siRNAs are RNA duplexes normally 15-30 nucleotides long that can associate with a cytoplasmic multi-protein complex known as RNAi-induced silencing complex (RISC). RISC loaded with siRNA mediates the degradation of homologous mRNA transcripts; therefore siRNA can be designed to knock down protein expression with high specificity. Unlike other antisense technologies, siRNA function through a natural mechanism evolved to control gene expression through non-coding RNA. This is generally considered to be the reason why their activity is more potent in vitro and in vivo than either antisense oligonucleotide or ribozymes.

RNAi reagents may include DNA sense:RNA antisense hybrids, RNA sense:DNA antisense hybrids, and DNA:DNA hybrids are capable of mediating RNAi. Thus, RNAi molecules comprising any of these different types of double-stranded molecules may be used. In addition, it is understood that RNAi molecules may be used and introduced to cells in a variety of forms. Accordingly, as used herein, RNAi molecules encompasses any and all molecules capable of inducing an RNAi response in cells, including, but not limited to, double-stranded polynucleotides comprising two separate strands, i.e. a sense strand and an antisense strand, e.g., small interfering RNA (siRNA); polynucleotides comprising a hairpin loop of complementary sequences, which forms a double-stranded region, e.g., shRNAi molecules, and expression vectors that express one or more polynucleotides capable of forming a double-stranded polynucleotide alone or in combination with another polynucleotide.

RNA interference (RNAi) may be used to specifically inhibit expression of target polynucleotides. Double-stranded RNA-mediated suppression of gene and nucleic acid expression may be accomplished according to the invention by introducing dsRNA, siRNA or shRNA into cells or organisms. siRNA may be double-stranded RNA, or a hybrid molecule comprising both RNA and DNA, e.g., one RNA strand and one DNA strand, or sisiRNA.

RNAi molecules targeting specific polynucleotides can be readily prepared according to procedures known in the art. Accordingly, one skilled in the art would understand that a wide variety of different siRNA molecules may be used to target a specific gene or transcript. In certain embodiments, siRNA molecules according to the invention are double-stranded and 16-30 or 18-25 nucleotides in length, including each integer in between.

Generally, siRNA molecules are completely complementary to one strand of a target DNA molecule. In other embodiments, siRNAs may have a modified composition, such as, for example, 2'-deoxy or 2'-O-methyl modifications. However, in preferred embodiments, the entire strand of the siRNA is not made with either 2' deoxy or 2'-O-modified bases.

In certain embodiments, the present invention relates to methods and compositions for producing lipid-encapsulated nucleic acid particles in which nucleic acids are encapsulated within a lipid layer. Such nucleic acid-lipid particles, incorporating siRNA oligonucleotides, are characterized using a variety of biophysical parameters including: (1) nucleic acid to lipid ratio; (2) encapsulation efficiency; and (3) particle size. High encapsulation efficiency, good nuclease resistance and serum stability and controllable particle size, generally less than 200 nm in diameter are desirable. In addition, the nature of the nucleic acid polymer is of significance, since the modification of nucleic acids in an effort to impart nuclease resistance adds to the cost of therapeutics while in many cases providing only limited resistance. Unless stated otherwise, these criteria are calculated in this specification as follows:

Nucleic acid to lipid ratio is the amount of nucleic acid in a defined volume of preparation divided by the amount of lipid in the same volume. This may be expressed as a mole per mole basis or on a weight per weight basis, or on a weight per mole basis. For final, administration-ready formulations, the nucleic acid:lipid ratio is calculated after dialysis, chromatography and/or enzyme (e.g., nuclease) digestion has been employed to remove as much of the external nucleic acid as possible.

Encapsulation

To determine siRNA encapsulation efficiency (EE), expressed as percent encapsulated siRNA in lipid-nucleic acid particles, a RiboGreen assay is utilized as follows. The procedure may be used to determine duplex and single-stranded RNA or DNA concentration in solution.

Equipment includes BioTek Instruments, Inc. FLx800, variable pipettes, and a vortex mixer. Reagents include RNAse-free water (MilliQ grade, or equivalent), 20×TE buffer "RNase free" (Invitrogen, T11493, or equivalent), Quant-iT RiboGreen Reagent (Invitrogen, R11491), and 10% Triton X-100 in water (Thermo Scientific, 28314, or equivalent).

Preparation of 1×TE Buffer involves transfer of 38 mL of RNAse-free water into a 50 mL centrifuge tube using a 50 mL graduated cylinder; and pipetting 2 mL of 20×TE Buffer solution into the centrifuge tube and mix using a vortexer.

Preparation of 2% Triton X-100 and 1% Triton X-100 in 1×TE Buffer, involves pipetting 2 mL or 1 mL, respectively, of 10% Triton X-100 into an RNase-free 15 mL conical tube, adding 8 mL or 9 mL, respectively, of 1×TE buffer, and swirling to mix well.

Preparation of a RiboGreen working solution, involves removing a frozen stock of RiboGreen Reagent warming to room temperature, and diluting 1:200 with TE buffer. The centrifuge tube is wrapped in aluminum foil to prevent any excess light from reaching the solution.

A standard is prepared by preparing a RNA solution in TE buffer, and plating into a 96 well plate. Samples are diluted to a final concentration of approximately 80 ng/mL siRNA and transferred to the 96 well plate as shown in FIGS. 1A and 1B. The RiboGreen working solution is added and mixed with each sample and standard. The samples are incubated in the dark for 1-2 minutes before analyzing.

1% Triton X-100 in TE buffer is then added to duplicate samples and RiboGreen working solution is then added.

Encapsulation efficiency is determined from the fluorescent measurements using the average of the fluorescence results from each sample, corrected for baseline measurements of the average of external samples (fluorescence of RiboGreen reagent in the absence of RNA), and after correcting for an 8% reduction in signal intensity due to the presence of Triton X-100. Encapsulation efficiency is then calculated using the following equation:

EE=(Triton sample−liposome sample)/(Triton sample)

That is, encapsulation efficiency is the difference between the total RNA value (measured after dissolving the liposome with detergent) and the intact liposome value, divided by the total RNA value. The fluorescence obtained from the intact liposome sample will consist of free RNA in solution plus the RNA absorbed on the outside surface of liposome.

Size

Size indicates the size (diameter) of the particles formed. Size distribution may be determined using a Malvern Zetasizer Nano-ZS dynamic light scattering (DLS) instrument.

This procedure applies to the measurement of the volume mean diameter, Z-average diameter, and polydispersity for in-process liposome samples. Polydispersity is a numerical value for particle size distribution.

Measurements are performed at room temperature. Samples and reagents should be equilibrated to room temperature. The volume-weighted mean particle diameter and polydispersity index is determined Method of Manufacture Preparation of Liposomes The lipid mixture can be solubilized in a water miscible organic solvent, preferably absolute ethanol. In most embodiments, the organic solvent is used in the form in which it is commercially available.

In one exemplary embodiment, the mixture of lipids is a mixture of cationic amino lipids, neutral lipids (other than an amino lipid), a steroid (e.g., cholesterol), and a PEG-modified lipid (e.g., a PEG-S-DMG, PEG-C-DOMG or PEGDMA) are co-solubilized in the organic solvent. In preferred embodiments, the lipid mixture consists essentially of a cationic amino lipid, a neutral lipid, cholesterol and a PEG-modified lipid. In further preferred embodiments, the lipid mixture consists of a cationic lipid, DOPE (or another helper lipid, with either an ionizable or a permanent cationic charge), cholesterol and PEG-conjugated lipid at various molar ratios. Preferred molar ranges are between 40 to 60 mole % cationic lipid, 10 to 30% neutral lipid, 20 to 40% cholesterol, and 1 to 10% PEG-modified lipid.

A targeting lipid can be added to the lipid mixture, e.g., diVA-PEG750-diVA (or other VA-conjugated targeting lipid) at molar ratio of 0.1 to 5 (targeting lipid:total lipid).

The total concentration of lipid is less than 25 mg/ml, preferably less than 5 mg/ml. The lipid mixture is filtered through membrane, e.g. a 0.45 or 0.2 μm filter.

In accordance with the invention, the lipid mixture is combined with a buffered aqueous solution. The buffered aqueous solution may be a solution in which the buffer has a pH less than the pKa of a protonated lipid in the lipid mixture. Examples of suitable buffers include citrate, phosphate, acetate, and MES. A particularly preferred buffer is citrate buffer. Preferred buffers will be in the concentration range of 1-1000 mM of the anion, depending on the chemistry of the nucleic acid being encapsulated, and optimization of buffer concentration may be significant to achieving high loading levels. Alternatively, pure water acidified to pH 5-6 with HCl, $H_2SO_4$, or the like, may be used. It may be suitable to add a cryoprotectant, and/or a non-ionic solute, which will balance the osmotic potential across the particle membrane, e.g., when the particles are dialyzed to remove ethanol, increase the pH, or mixed with a pharmaceutically acceptable carrier such as normal saline. The amount of nucleic acid in buffer is from about 0.08 to 0.8 mg/mL.

At the time of addition of ethanol, the temperature of the aqueous solution is 25 to 45° C., preferably 30 to 40° C. The ethanol solution is added to the aqueous solution either by spraying on the air-water interface, in a narrow stream, or through a liquid-liquid interface between ethanol delivered through a tube that is submerged in the aqueous solution.

The organic solution is added by gravity or by a pump delivering the organic solution to the aqueous solution at a controlled rate, preferably a constant rate. The delivery of the organic solution can be completed in 1 minute to 100 minutes, preferably in 5 to 25 minutes. The organic solution may be added through a single spray or stream, through a tube or nozzle, or through a multi-nozzle system. While the organic solution is added into the aqueous solution, the resulting solution it may be mixed by stirring, shaking, or recirculation. The addition step results in a final concentration that is preferably 25 to 45% ethanol, most preferably 35% ethanol.

The final solution is treated to remove the organic solvent, by dialysis or filtration, preferably by diafiltration. While the ethanol is removed, the aqueous solution is converted to a one buffered at a neutral pH, pH 6.8 to pH 7.5, preferably, pH 7.2, for example a phosphate buffer. The resulting aqueous solution is preferably sterilized before storage or use, e.g., by filtration through a 0.22 μm filter.

Liposomes Encapsulating Negatively Charged Therapeutic Polymers

The methods described herein are useful for preparing lipid particles with a negatively charged therapeutic polymer, e.g., an RNA molecule. In the methods described herein, a mixture of lipids is combined with an aqueous solution of the polymer. The polymer is efficiently encapsulated in the resulting lipid particles.

The total charge of the negatively charged polymer must be less than or equal to the number of positive charges in the lipid mixture at the time of addition (at least 1:1, lipid:polymer), preferable 2:1, more preferably 2.5:1. For example, when RNA is used, the encapsulated nucleic acids are present in a nucleic acid/lipid ratio of 14:1 to 8:1, wt:wt.

When the mixture of lipids comprises a cationic lipid with a charge, lipid vesicles may be formed in the presence of negatively charged polymer to encapsulate and entrap the polymer. The resulting particles can be neutralized by increasing the pH of the medium to physiological pH or higher. The vesicles formed in this manner provide formulations of uniform vesicle size with high content of nucleic acids.

In either instance, the vesicles encapsulating the polymer (nanoparticles) have a size range of from 50 to 150 nm.

The lipid mixture is prepared as described above, in the previous section entitled "Preparation of liposomes."

In accordance with the method described herein, the lipid mixture is combined with a buffered aqueous solution that may contain the negatively charged polymer. The buffered aqueous solution of may be a solution in which the buffer has a pH of less than the pKa of a protonated lipid in the lipid mixture. Examples of suitable buffers include citrate, phosphate, acetate, and MES. A particularly preferred buffer is citrate buffer. Preferred buffers will be in the range of 1-1000 mM of the anion, depending on the chemistry of the polymer being encapsulated, and optimization of buffer concentration may be significant to achieving high loading levels.

Alternatively, pure water acidified to pH 5-6 with HCl, $H_2SO_4$ or the like may be useful. In this case, it may be suitable to add a cryoprotectant and/or a non-ionic solute which will balance the osmotic potential across the particle membrane when the particles are dialyzed to remove ethanol, increase the pH, or mixed with a pharmaceutically acceptable carrier such as normal saline.

For RNA, a schematic of the process described herein is depicted in FIGS. 1A and 1B. Solutions are prepared by dissolution of lyophilized or solid material in water, preferably buffered at pH 3.5-4.5, for example with 50 mM citrate. The amount of nucleic acid in buffer is from 0.08 to 0.8 mg/mL. At the time of addition of ethanol, the temperature of the aqueous solution is 25 to 45° C., preferably 30 to 40° C. If single stranded nucleic acid is used, briefly heating at elevated temperature may be useful, e.g., 1-2 minutes at 65° C.

The ethanol solution is added to the aqueous solution either by spraying on the air-water interface, in a narrow stream, or through a liquid-liquid interface between ethanol delivered through a tube that is connected to a container with the aqueous solution.

The organic solution is added by delivering the organic solution to the aqueous solution at a controlled rate, preferably at a constant rate. The delivery of the organic solution can be completed in 1 minute to 100 minutes, preferably in 5 to 25 minutes. The organic solution may be added through a single spray or stream, through a tube or nozzle, or through a multinozzle system. While the organic solution is added into the aqueous solution, the resulting solution may be mixed by stirring, shaking, or recirculation. The addition step results in a final concentration sufficient to disrupt the liposomal bilayer structure, preferably 25 to 45% ethanol, most preferably 35% ethanol.

For lipid-nucleic acid particles, the final RNA concentration is 0.05 to 0.5 mg/ml. The final ratio, lipid:RNA, is 14:1 to 8:1 w:w (2.5:1, charge:charge).

The final solution is treated to remove the organic solvent, by dialysis or filtration, preferably by diafiltration. While the ethanol is removed, the aqueous solution is converted to a one buffered at a neutral pH, pH 6.8 to pH 7.5, preferably, pH 7.2, for example a phosphate buffer. The resulting aqueous solution is preferably sterilized before storage or use, e.g., by filtration through a 0.22 µm filter.

The final encapsulation efficiency is greater than 90%. The final mean particle diameter is 50 to 150 nm. The polydispersity index (PDI) is less than 0.2. The Zeta potential is greater than 30 mV.

Pharmaceutical Compositions

The lipid particles of present invention, particularly when associated with a therapeutic agent, may be formulated as a pharmaceutical composition, e.g., which further comprises a pharmaceutically acceptable diluent, excipient, or carrier, such as physiological saline or phosphate buffer, selected in accordance with the route of administration and standard pharmaceutical practice.

In particular embodiments, pharmaceutical compositions comprising the lipid-nucleic acid particles of the invention are prepared according to standard techniques and further comprise a pharmaceutically acceptable carrier. Generally, normal saline will be employed as the pharmaceutically acceptable carrier. Other suitable carriers include, e.g., water, buffered water, 0.9% saline, 0.3% glycine, a sugar or polysaccharide, e.g., sucrose and/or trehalose, and the like, including glycoproteins for enhanced stability, such as albumin, lipoprotein, globulin. Bulking agents, cyro-protectants and/or lyoprotectants, as well as metal scavengers, e.g., EDTA, may be included. In compositions comprising saline or other salt containing carriers, the carrier is preferably added following lipid particle formation. Thus, after the lipid-nucleic acid compositions are formed, the compositions can be diluted into pharmaceutically acceptable carriers such as normal saline.

The resulting pharmaceutical preparations may be sterilized by conventional, well known sterilization techniques. The aqueous solutions can then be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the lipidic suspension may include lipid-protective agents which protect lipids against free-radical and lipid peroxidative damages on storage. Lipophilic free-radical quenchers, such as a-tocopherol and water-soluble iron-specific chelators, such as ferrioxamine, are suitable.

The concentration of lipid particle or lipid-nucleic acid particle in the pharmaceutical formulations can vary widely, i.e., from less than about 0.01%, usually at or at least about 0.05-5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, complexes composed of irritating lipids may be diluted to low concentrations to lessen inflammation at the site of administration. In one group of embodiments, the nucleic acid will have an attached label and will be used for diagnosis (by indicating the presence of complementary nucleic acid). In this instance, the amount of complexes administered will depend upon the particular label used, the disease state being diagnosed and the judgment of the clinician but will generally be between about 0.01 and about 50 mg per kilogram of body weight, preferably between about 0.001 and about 5 mg/kg of body weight.

Method of Use

The lipid particles described herein may be used to deliver a nucleic acid to a cell, in vitro or in vivo. While the following description of various methods of using the lipid particles and related pharmaceutical compositions of the present invention are exemplified by description related to nucleic acid-lipid particles, it is understood that these methods and compositions may be readily adapted for the delivery of any therapeutic agent for the treatment of any disease or disorder that would benefit from such treatment.

In certain embodiments, the present invention provides methods for introducing a nucleic acid into a cell. Preferred nucleic acids for introduction into cells are siRNA, immune-stimulating oligonucleotides, plasmids, antisense and ribozymes. These methods may be carried out by contacting the particles or compositions of the present invention with the cells for a period of time sufficient for intracellular delivery to occur.

The compositions of the present invention can be adsorbed to almost any cell type. Once adsorbed, the nucleic acid-lipid particles can either be endocytosed by a portion of the cells, exchange lipids with cell membranes, or fuse with the cells. Transfer or incorporation of the nucleic acid portion of the complex can take place via any one of these pathways. Without intending to be limited with respect to the scope of the invention, it is believed that in the case of particles taken up into the cell by endocytosis the particles then interact with the endosomal membrane, resulting in destabilization of the endosomal membrane, possibly by the formation of nonbilayer phases, resulting in introduction of the encapsulated nucleic acid into the cell cytoplasm. Similarly in the case of direct fusion of the particles with the cell plasma membrane, when fusion takes place, the liposome membrane is integrated into the cell membrane and the contents of the liposome combine with the intracellular fluid. Contact between the cells and the lipid-nucleic acid compositions, when carried out in vitro, will take place in a biologically compatible medium. The concentration of compositions can vary widely depending on the particular application, but is generally between 1 µmol and 10 mmol. In certain embodiments, treatment of the cells with the lipid-nucleic acid compositions will generally be carried out at physiological temperatures (37° C.) for periods of time from 1 to 24 hours, preferably from 2 to 8 hours. For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

In one group of embodiments, a lipid-nucleic acid particle suspension is added to 60-80% confluent plated cells having a cell density of from about 103 to about $10^5$ cells/mL, more preferably about $2 \times 10^4$ cells/mL. The concentration of the suspension added to the cells is preferably of from about 0.01 to 20 µg/mL, more preferably about 1 µg/mL.

Typical applications include using well known procedures to provide intracellular delivery of siRNA to knock down or silence specific cellular targets. Alternatively applications include delivery of DNA or mRNA sequences that code for therapeutically useful polypeptides.

Methods of the present invention may be practiced in vitro, ex vivo, or in vivo. For example, the compositions of the present invention can also be used for deliver of nucleic acids to cells in vivo, using methods which are known to those of skill in the art.

For in vivo administration, the pharmaceutical compositions are preferably administered parenterally, i.e., intraarticularly, intravenously, intraperitoneally, subcutaneously, or intramuscularly. In particular embodiments, the pharmaceutical compositions are administered intravenously or intraperitoneally by a bolus injection.

In other methods, the pharmaceutical preparations may be contacted with the target tissue by direct application of the preparation to the tissue. The application may be made by topical, "open" or "closed" procedures. By "topical," it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The lipid-nucleic acid compositions can also be administered in an aerosol inhaled into the lungs or by direct injection at the site of disease.

The methods of the present invention may be practiced in a variety of subjects or hosts. Preferred subjects or hosts include mammalian species, such as humans, non-human primates, dogs, cats, cattle, horses, sheep, and the like. In particular embodiments, the subject is a mammal, such as a human, in need of treatment or prevention of a disease or disorder, e.g., a subject diagnosed with or considered at risk for a disease or disorder.

Dosages for the lipid-therapeutic agent particles of the present invention will depend on the ratio of therapeutic agent to lipid and the administrating physician's opinion based on age, weight, and condition of the patient.

In one embodiment, the present invention provides a method of modulating the expression of a target polynucleotide or polypeptide. These methods generally comprise contacting a cell with a lipid particle of the present invention that is associated with a nucleic acid capable of modulating the expression of a target polynucleotide or polypeptide. As used herein, the term "modulating" refers to altering the expression of a target polynucleotide or polypeptide. In different embodiments, modulating can mean increasing or enhancing, or it can mean decreasing or reducing. Methods of measuring the level of expression of a target polynucleotide or polypeptide are known and available in the arts and include, e.g., methods employing reverse transcription-polymerase chain reaction (RT-PCR) and immunohistochemical techniques. In particular embodiments, the level of expression of a target polynucleotide or polypeptide is increased or reduced by at least 10%, 20%, 30%, 40%, 50%, or greater than 50% as compared to an appropriate control value.

For example, if increased expression of a polypeptide desired, the nucleic acid may be an expression vector that includes a polynucleotide that encodes the desired polypeptide. On the other hand, if reduced expression of a polynucleotide or polypeptide is desired, then the nucleic acid may be, e.g., an antisense oligonucleotide, siRNA, or microRNA that comprises a polynucleotide sequence that specifically hybridizes to a polynucleotide that encodes the target polypeptide, thereby disrupting expression of the target polynucleotide or polypeptide. Alternatively, the nucleic acid may be a plasmid that expresses such an antisense oligonucleotide, siRNA, or microRNA.

In particular embodiments, the nucleic acid active agent or therapeutic agent is selected from an siRNA, a microRNA, an antisense oligonucleotide, and a plasmid capable of expressing an siRNA, a microRNA, or an antisense oligonucleotide, and in which the siRNA, microRNA, or antisense RNA comprises an oligonucleotide that specifically binds to a polynucleotide that encodes the polypeptide, or a complement thereof, such that the expression of the polypeptide is reduced.

In other embodiments, the nucleic acid is a plasmid that encodes the polypeptide or a functional variant or fragment thereof, such that expression of the polypeptide or the functional variant or fragment thereof is increased.

In related embodiments, the present invention provides a method of treating a disease or disorder characterized by overexpression of a polypeptide in a subject, comprising providing to the subject a pharmaceutical composition of the present invention, in which the therapeutic agent is selected from an siRNA, a microRNA, an antisense oligonucleotide, and a plasmid capable of expressing an siRNA, a microRNA, or an antisense oligonucleotide, and in which the siRNA, microRNA, or antisense RNA comprises an oligonucleotide that specifically binds to a polynucleotide that encodes the polypeptide, or a complement thereof.

In another related embodiment, the present invention includes a method of treating a disease or disorder characterized by underexpression of a polypeptide in a subject, comprising providing to the subject a pharmaceutical composition of the present invention, in which the therapeutic agent is a plasmid that encodes the polypeptide or a functional variant or fragment thereof.

EXAMPLES

Example 1

Liposome/RNA nanoparticles and lipid only nanoparticles were prepared by reference to FIGS. 1A and 1B at various scales ranging from 20 L to 200 L using 2 different siRNAs.

A stock lipid solution was mixed as follows. All lipid components (cationic lipid, DOPE, cholesterol, PEG conjugated lipids, and diVA-PEG750-diVA were dissolved in absolute ethanol to a weight concentration of 4.5 mg/mL. Lipids in ethanol were raised to 35 to 40° C. and mixed until visibly dissolved.

The lipid solution was pumped from the Lipid Stock vessel through a 0.45/0.22 µm Filter to a Filtered Lipid Stock vessel.

The siRNA was solubilized in 50 mM citrate buffer in a siRNA Stock vessel at a concentration 0.26 mg/mL or 0.16 mg/ml depending on the final siRNA to lipid ratio. The siRNA solution was pumped from the siRNA Stock vessel through a 0.45/0.22 µm Filter to a Liposomal siRNA in 35% Ethanol vessel.

The Liposomal siRNA in 35% Ethanol vessel was brought to 35 to 40° C. while continuously stirring the contents. The lipid solution was sprayed on the surface of the siRNA containing buffer using a nozzle to spontaneously form siRNA loaded liposomes. Lipids were combined with siRNA to reach a final total lipid to siRNA ratio of either 14:1 or 9:1 (wt:wt) and an ethanol concentration of 35%.

The liposome solution was then diluted with 0.22 µm filtered PBS buffer into a 20 liter Flex Boy single use bag to a final ethanol concentration of approximately 10%. The resulting liposome solution was concentrated and then diafiltered against 10× volumes of PBS to remove ethanol and exchange the buffer. The entire concentration and diafiltration steps were carried out using a Quattro Flow (diaphragm) pump mounted with a single use pump chamber, single use flexible tubing, and single use hollow-fiber membrane cartridges. The final suspension was filtered through 0.45/0.22 µm Filter for bioburden reduction into a final single use collection bottle. The results are shown in Table 1.

TABLE 1

| Batch Vol [L] | Drug Substance | Lipid:Drug [wt/wt] | Particle Size | | EE [%] | Product Yield [siRNA recovery] |
| --- | --- | --- | --- | --- | --- | --- |
| | | | Mean [nm] | PDI | | |
| 20 | siRNA 1 | 14:1 | 79.6 | 0.144 | 95% | >90% |
| 20 | Empty Liposomes (no siRNA) | na | 78.1 | 0.129 | na | >90% |
| 20 | siRNA 2 | 9:1 | 88.8 | 0.156 | 92% | >90% |
| 50 | siRNA 2 | 14:1 | 80.2 | 0.146 | 94% | >90% |
| 120 | Empty Liposomes (no siRNA) | na | 79.1 | 0.107 | na | >90% |
| 120 | siRNA 2 | 9:1 | 89.9 | 0.138 | 92% | >90% |
| 200 | siRNA 1 | 14:1 | 89.1 | 0.154 | 94% | >90% |
| 200 | siRNA 2 | 14:1 | 83.7 | 0.143 | 94% | >90% |

Preparation of Liposomes

In one exemplary embodiment, the mixture of lipids is a mixture of cationic amino lipids, neutral lipids (other than an amino lipid), a steroid (e.g., cholesterol), and a PEG-modified lipid (e.g., a PEG-S-DMG, PEG-C-DOMG or PEGDMA) are co-solubilized in the organic solvent. In preferred embodiments, the lipid mixture consists essentially of a cationic amino lipid, a neutral lipid, cholesterol and a PEG-modified lipid. In further preferred embodiments, the lipid mixture consists of a cationic lipid, DOPE (or another helper lipid, with either an ionizable or a permanent cationic charge), cholesterol and PEG-conjugated lipid at various molar ratios. Preferred molar ranges are between 40 to 60 mole % cationic lipid, 10 to 30% neutral lipid, 20 to 40% cholesterol, and 1 to 10% PEG-modified lipid. A targeting lipid can be added to the lipid mixture, e.g., diVA-PEG750-diVA (or other VA-conjugated targeting lipid) at molar ratio of 0.1 to 5 (targeting lipid:total lipid). The lipid mixture may also include a mixture of polymers or processing aids which can be of natural (e.g., chitosan) or synthetic (e.g. PEI) origin. The total concentration of lipid is less than 25 mg/ml, preferably less than 5 mg/ml. The lipid mixture is filtered through membrane, e.g. a 0.45 or 0.2 µm filter.

In accordance with the invention, the lipid mixture is combined with a buffered aqueous solution. The buffered aqueous solution may be a solution in which the buffer has a pH less than the pKa of a protonatable lipid in the lipid mixture. Examples of suitable buffers include citrate, phosphate, acetate, and MES. A particularly preferred buffer is citrate buffer. Preferred buffers will be in the concentration range of 1-1000 mM of the anion, depending on the chemistry of the nucleic acid being encapsulated, and optimization of buffer concentration may be significant to achieving high loading levels. Alternatively, pure water acidified to pH 5-6 with HCl, $H_2SO_4$, or the like, may be used. It may be suitable to a non-ionic solute which will balance the osmotic potential across the particle membrane, e.g., when the particles are dialyzed to remove ethanol, increase the pH, or mixed with a pharmaceutically acceptable carrier such as normal saline. Buffer may also include processing aids (e.g. poloxamers, surfactants, detergents), bulking agents (e.g., mannitol) or cryoprotectants (e.g., sucrose, trehalose, galactose, inulin). The amount of nucleic acid in buffer is from about 0.08 to 0.8 mg/mL.

At the time of addition of ethanol, the temperature of the aqueous solution and ethanol is 25 to 45° C., preferably 30 to 40° C. The ethanol solution is added to the aqueous solution through a liquid-liquid interface and the ethanol is delivered through a tube or nozzle that is submerged in the aqueous solution.

The organic solution is added by a pump delivering the organic solution to the aqueous solution at a controlled rate, preferably a constant rate. The delivery of the organic solution can be completed in 1 minute to 100 minutes, preferably in 2 to 20 minutes. The organic solution may be added through a single orifice or nozzle, or through a multi-orifice or nozzle system. Orifice diameter of the single (or multinozzle array) may be from 10 to 1000 μm, preferably from 300 to 600 μm. Addition may be performed by applying from 0 to 30 psi to the organic stream to aid in dispersion. While the organic solution is added into the aqueous solution, the resulting solution is mixed by stirring or recirculation. The addition step results in a final concentration that is preferably 25 to 45% ethanol, most preferably 35% ethanol.

The final solution is treated to remove the organic solvent, by dialysis or preferably by diafiltration. While the ethanol is removed, the aqueous solution is converted to one buffered at a neutral pH, pH 6.8 to pH 7.5, preferably, pH 7.2, for example a phosphate buffer. Buffer may also include processing aids (e.g. poloxamers, surfactants, detergents), bulking agents (e.g., mannitol) or cryoprotectants (e.g., sucrose, trehalose, galactose, inulin). The resulting aqueous solution is preferably sterilized before storage or use, e.g., by filtration through a 0.22 μm filter.

This method of liposome production can be used in connection with a manifold SUS comprising a system of SUS sub-units. This manifold system may be comprised of the following sub-units: a lipid mixing unit consisting of a lipid mixing bag for preparing a lipid solution in a water-miscible organic solvent, a lipid holding bag, and a means of transferring the lipid solution from the lipid unit to the lipid holding unit; a RNA mixing unit consisting of a RNA mixing bag for preparing a RNA solution, a RNA holding bag, and a means of transferring the RNA solution from the RNA unit to the RNA holding unit; a means of transferring the lipid solution from the lipid holding bag to the RNA solution; and a diafiltration system consisting of hollow fiber membranes, a single use diaphragm pump head, and various holding bags.

The SUS equipment can be pre-sterilized and operated using sterile connections/disconnections to produce liposomes using an aseptic process. Aseptic processing eliminates the requirement of final sterile (0.22 μm) filtration. Absence of the 0.22 μm filter allows a greater range of particle sizes (>200 nm) to be processed and solves any possible filter/drug product compatibility issues.

Example 2

Effect of Concentration on RNA-Lipid Particle Size

This example describes the effect of siRNA and lipid concentration on particle size.

To prepare nanoparticles by the method described herein. A cationic lipid, DOPE, cholesterol, a PEG-BML, and diVA-PEG750-diVA were solubilized in absolute ethanol at a molar ratio of 50:10:38:2:5, respectively. The siRNA was solubilized in 50 mM citrate buffer at pH 4.5.

A siRNA-containing buffer was brought to 35 to 40° C. while continuously stirring in a mixing vessel. The ethanol/lipid mixture was then sprayed onto the surface of the siRNA containing buffer using a manifold/nozzle array to spontaneously form siRNA loaded liposomes. Lipid and RNA concentrations were adjusted to reach a final siRNA concentration range from 0.05 to 0.5 mg/mL, a drug:lipid ratio of 0.08 (wt:wt), and an ethanol concentration of 35%. The lipid to siRNA ratio was kept constant for all conditions tested.

The siRNA loaded liposomes were diluted to ~10% ethanol to stabilize the particles and then diafiltered against 10× volumes of PBS (pH 7.2) to remove ethanol and exchange the buffer. Final product was filtered through 0.22 μm, sterilizing grade, PES filter for bioburden reduction. Volume, mean particle size and polydispersity index (PDI) were determined using dynamic light scattering (DLS). The results are shown in the Table 2.

TABLE 2

| Final | Vol. Mean Diam. [nm] | | |
|---|---|---|---|
| siRNA | Mean | SD | PDI |
| 0.05 | 96.7 | 7.0 | 0.084 |
| 0.10 | 105.7 | 10.1 | 0.073 |
| 0.25 | 116.8 | 8.4 | 0.125 |
| 0.50 | 141.9 | 10.0 | 0.105 |

The results show that particle size increases with increasing siRNA concentration (in mg/ml). Reducing the lipid and siRNA concentrations (keeping the same relative ratio) reduces particles size, while increasing concentration increases particle size. Final siRNA concentrations between 0.05 to 0.5 mg/ml produce nanoparticles with a mean particle diameter of 96.7 to 141.9 nm, less than 150 nm, and with a polydispersity index less than 0.2 in all cases.

Particles size less than 150 nm with a PDI less than 0.2 are produced by the method described herein, without preparing empty preformed lipid vesicles and/or without mechanical processing.

Example 3

Effect of Process Parameters on RNA-Lipid Particle Formation

This example describes the effect of various process parameters on RNA-Lipid particle formation. Several parameters were screened during this experiment, including temperature, ethanol concentration, buffer, lipid:siRNA ratio, and the nozzle type used to disperse the lipid solution.

HEDC, DOPE, cholesterol, a PEG-BML, and diVA-PEG750-diVA were dissolved in absolute ethanol of at a molar ratio of 40:30:25:5:2. The siRNA containing buffer was brought to the indicated temperature while continuously stirring in a mixing vessel. The ethanol/lipid mixture was then sprayed onto the surface of the siRNA containing buffer using a nozzle to spontaneously form siRNA loaded liposomes. Lipids were combined with siRNA to reach a final siRNA concentration of 0.1 mg/mL at the indicated drug/lipid ratio and the indicated the final ethanol percentage.

The siRNA was solubilized in citrate buffer that was varied in strength from 25 to 100 mM and pH 3.5 to pH 6.5. The mixture temperature was varied from 25 to 45° C. The final ethanol concentration varied from 25 to 45%. The drug:lipid ratio (wt/wt) varied from 0.07 to 0.11. The hydration nozzle inner diameter (ID) varied from 0.005 to 0.125 inches. Each condition was performed as a measurement to compare the effect of each process parameter. Unless indicated each condition was performed at with 50 mM citrate buffer, pH 4.5, 35° C., 35% final ethanol, drug:lipid ratio of 0.07, and nozzle ID of 0.005 inches.

The siRNA loaded liposomes were diluted to 10% ethanol to stabilize the particles and then diafiltered against 10× volumes of PBS (pH 7.2) to remove ethanol and exchange the buffer. Final product was filtered through 0.22 µm, sterilizing grade, PES filter for bioburden reduction.

Table 3 show the effect of pH on the mean diameter and PDI of the lipid-nucleic acid nanoparticles. Increasing buffer pH resulted in increasing particle size, albeit less than 150 nm mean particle size.

TABLE 3

| Buffer pH | Vol. Mean Diam. [nm] | | |
|---|---|---|---|
| | Mean | SD | PDI |
| 6.5 | 130.7 | 17.7 | 0.111 |
| 4.5 | 108.5 | 7.1 | 0.163 |
| 3.5 | 86.1 | 10.2 | 0.149 |

Table 4 shows the effect of buffer concentration on various parameters. The results showed that increasing buffer concentration reduced siRNA recovery. The mean particle diameter and PDI appeared unaffected. Minimum particle size was observed for pH 3.5 and maximum siRNA recovery was observed for 25 mM citrate buffer.

TABLE 4

| Buffer Conc. | Vol. Mean Diam. [nm] | | | EE | siRNA |
|---|---|---|---|---|---|
| [mM] | Mean | SD | PDI | [%] | Recovery [%] |
| 25 | 103.1 | 13.4 | 0.179 | 96 | 94 |
| 50 | 113.8 | 15.5 | 0.156 | 94 | 87 |
| 100 | 101.0 | 9.4 | 0.185 | 94 | 80 |

Table 5 shows that increasing hydration temperature from 25 to 45° C. decreased particle size from 135.7 to 102.2 nm while improving siRNA recovery from 80% to 87%. Increasing final ethanol percentage increased particle size with no effect on siRNA recovery, but reduced encapsulation efficiency to 88%.

TABLE 5

| Hydration Temp [° C.] | Final % EtOH | Vol. Mean Diam. [nm] | | | EE [%] | siRNA Recovery [%] |
|---|---|---|---|---|---|---|
| | | Mean | SD | PDI | | |
| 25 | 35 | 135.7 | 15.9 | 0.057 | 95 | 80 |
| 35 | 25 | 103.8 | 9.8 | 0.178 | 94 | 84 |
| 35 | 35 | 113.8 | 15.5 | 0.156 | 94 | 87 |
| 35 | 45 | 130.8 | 11.7 | 0.136 | 88 | 86 |
| 45 | 35 | 102.2 | 3.4 | 0.182 | 93 | 87 |

Table 6 shows that increasing the drug:lipid ratio decreased, siRNA recovery increased from 80 to 87%. Maximum recovery was observed at a ratio of 0.07 drug:lipid (w:w). All other measured properties were unaffected by drug:lipid ratio. This result is surprising and unexpected in view of the disclosure of Maurer et al. and Semple et al., who both describe optimal recovery is at drug:lipid (w:w) equal to or greater than 0.16 (lipid:drug (w:w) equal to or less than 6.25). The current results suggest an opposite trend is obtained using the method described herein.

TABLE 6

| Lipid:siRNA | Vol. Mean Diam. [nm] | | | EE | siRNA |
|---|---|---|---|---|---|
| [wt/wt] | Mean | SD | PDI | [%] | Recovery |
| 9:1 | 93.9 | 17.6 | 0.186 | 95 | 80 |
| 12:1 | 85.6 | 14.0 | 0.218 | 95 | 82 |
| 14:1 | 113.8 | 15.5 | 0.156 | 94 | 87 |

Table 7 shows that increasing nozzle ID by 25 times did not impact particle size, encapsulation efficiency or siRNA recovery. There is substantial flexibility in the nozzle orifice being used to add the ethanol/lipids to the buffer surface. This flexibility could provide a major advantage during scale up.

TABLE 7

| Nozzle ID | Vol. Mean Diam. [nm] | | | EE | siRNA |
|---|---|---|---|---|---|
| [inch] | Mean | SD | PDI | [%] | Recovery |
| 0.005 | 105.2 | 5.8 | 0.119 | 98 | 81 |
| 0.050 | 100.7 | 11.7 | 0.124 | 96 | 87 |
| 0.125 | 109.7 | 13.3 | 0.097 | 96 | 81 |

Example 4

Comparison of Described Process to Referenced Methods for Batch Production of Liposomes These results compared the process described herein for preparing lipid/nucleic acid particles to the method described by Semple, et al. U.S. Pat. No. 6,858,225 (control method or control composition used by the control method) were prepared according to the composition of Example 3 or using the control method.

The composition of Example 3 consisted of a cationic lipid, DOPE, cholesterol, PEG conjugated lipid, and targeting lipid co-solubilized at a molar ratio of 40:30:25:5:2 (see Example 2, above).

The control composition consisted of DODAP, DSPC, cholesterol, and PEG-CER-14, co-solubilized at a molar ratio of 25:20:45:10.

In the method of Example 3, lipids were solubilized at 4.32 mg/ml in absolute ethanol, and siRNA was solubilized at 0.163 mg/ml in 50 mM citrate, pH 4.5. The siRNA solution was brought to 35 to 40° C. while continuously stirring in a mixing vessel. The ethanol/lipid mixture was then sprayed onto the surface of the siRNA containing buffer using a manifold/nozzle array. The final ethanol concentration was 35% and the final lipid/siRNA ratio was 14:1 (w:w). The resulting particles were then diluted to 10% ethanol and then diafiltered against 10× volumes of PBS (pH 7.2).

In the control method, lipids were solubilized at 25 mg/ml in absolute ethanol, and siRNA was solubilized at 4.17 mg/ml in 300 mM citrate, pH 4.0. The siRNA containing buffer was kept at room temperature while continuously stirring in a mixing vessel. The ethanol/lipid mixture was then sprayed onto the surface of the siRNA containing buffer using a single nozzle to spontaneously form siRNA loaded liposomes. The final ethanol concentration was 40%, and the final lipid/siRNA ratio was 6:1 (wt:wt). After mixing, the lipid/siRNA suspension was transferred into a 10 mL extruder prepared with two, 100 nm polycarbonate membranes and pre-equilibrated at 65° C. The suspension was extruded using ten passes at 300 psi. The resulting particles were diafiltered against 10× volumes of PBS, pH 7.2.

The particles resulting from each method were passed through a 0.22 μm filter. Mean particle size, PDI, and EE were measured as described herein.

The method of Example 3 produced smaller lipid nanoparticles than the control method without the extrusion step. The size of the particles produced by the control method was measured before extrusion. Particles prepared from the NDT-0009 composition using the control method had a mean particle size of greater than 250 nm particles. After extrusion and diafiltration the mean particle size reduced to 128 nm. The method of Example 3 produced particles with a mean particle size less than 150 nm without extrusion. A similar trend was observed starting with the control composition.

The method of Example 3 was more efficient at encapsulating siRNA into the lipid nanoparticles than the control method. The encapsulation efficiency (EE) of the particles prepared by the method of Example 3 is higher than those of particles formed by the control method (measured prior to diafiltration in both products). The EE of particles prepared by the Method of Example 3 are greater than 95% higher than those found for particles formed by the control method. In the control method, much of the free siRNA is removed after diafiltration which results in an improvement in EE of the final product.

The method of Example 3 produces nanoparticles with higher encapsulation efficiency than the control method. Final recovery of siRNA by the method of Example 3 was more than twice that obtains by the control method (72% vs. 33%), as measured after diafiltration in both products. These data reflect the improvement in EE as well as the lack of an extrusion step in the method of Example 3. The method of Example 3 provides better siRNA recovery because the extra extrusion step of the control method structurally changes the liposomes, and apparently dissociates siRNA from the particles. These results show that the method described herein provides several advantages over the control method by reducing the number of process steps while improving encapsulation efficiency and yield of nanoparticles with a mean particle size less than 150 nm.

Example 5

Comparison of Variability During Scale-Up of Liposome Batch Production

The process as described in Example 3 was performed with a different lipid composition that included the combination of a permanently charged (HEDC) cationic lipid and an ionizable (S104) cationic lipid molecule. HEDC, S104, DOPE, cholesterol, a PEG-BML, and diVA-PEG750-diVA were dissolved in absolute ethanol of at a molar ratio of 20:20:30:25:5:2. During scale-up different siRNA molecules, different batch volumes, and different siRNA (drug)/lipid ratios were evaluated. Table 8 summarizes the results of characterizing the nanoparticles resulting from the range of conditions.

TABLE 8

| Batch Vol [L] | Drug Substance | drug/lipid [wt/wt] | Particle size [nm] | PDI | EE [%] | Product Yield [siRNA recovery] |
|---|---|---|---|---|---|---|
| 5 | siRNA 1 | 0.07 | 93 | 0.14 | 97% | >90% |
| 20 | siRNA 1 | 0.07 | 83 | 0.15 | 95% | >90% |
| 20 | Empty Liposomes (no siRNA) | na | 83 | 0.14 | na | na |
| 20 | siRNA 2 | 0.11 | 90 | 0.16 | 92% | >90% |
| 50 | siRNA 2 | 0.07 | 82 | 0.14 | 94% | >90% |
| 120 | Empty Liposomes (no siRNA) | na | 86 | 0.14 | na | na |
| 120 | siRNA 2 | 0.11 | 82 | 0.14 | 94% | >90% |
| 200 | siRNA 1 | 0.07 | 86 | 0.17 | 94% | >90% |
| 200 | siRNA 2 | 0.07 | 86 | 0.17 | 96% | >90% |

The results show that the method described herein is quite robust. Similar particle size and PDI were obtained during a scale up spanning a 50-fold range. Particle size is consistently less than 100 nm, with >90% product yields. Polydispersity index values are in a very low range, indicating a nearly monodisperse population of vesicles.

Example 6

Comparison of Variability During Scale-Up of Liposome Batch Production for Sucrose Containing Formulations The process as described in Example 3 was performed with HEDC, S104, DOPE, cholesterol, a PEG-BML, and diVA-PEG750-diVA dissolved in ethanol at a molar ratio of 20:20:30:25:5:2. Sucrose was included in the preparation of the vesicles as described herein. Different batch volumes were evaluated and subject to freeze-thawing. Table 9 summarizes the results of characterizing the nanoparticles resulting from a range of conditions.

TABLE 9

Frozen (sucrose containing) formulations prepared using semi Single-use manufacturing train

| Batch Vol [L] | Drug Substance | drug/lipid [wt/wt] | Before Freezing | | | After Thawing | | | Product Yield [siRNA recovery] |
|---|---|---|---|---|---|---|---|---|---|
| | | | Size [nm] | PDI | EE [%] | Size [nm] | PDI | EE [%] | |
| 5 | siRNA 2 | 0.11 | 94 | 0.12 | 95 | 96 | 0.14 | 93 | >90% |
| 20 | siRNA 2 | 0.11 | 98 | 0.15 | 94 | 97 | 0.16 | 90 | >90% |

TABLE 9-continued

Frozen (sucrose containing) formulations prepared using semi Single-use manufacturing train

| Batch Vol [L] | Drug Substance | drug/lipid [wt/wt] | Before Freezing | | | After Thawing | | | Product Yield [siRNA recovery] |
|---|---|---|---|---|---|---|---|---|---|
| | | | Size [nm] | PDI | EE [%] | Size [nm] | PDI | EE [%] | |
| 120 | siRNA 2 | 0.11 | 96 | 0.14 | 90 | 96 | 0.14 | 89 | >90% |
| 120 | siRNA 2 | 0.11 | 97 | 0.15 | 91 | 99 | 0.15 | 89 | >90% |
| 120 | siRNA 2 | 0.11 | 100 | 0.15 | 91 | tbd | tbd | tbd | >90% |

The results show that freeze thawing did not change the properties of the lipid nanoparticles. The results also showed that variability between batches is quite low and that the process reproducibly produces uniform nanoparticles.

Conditions have been established for the stabilization of drug:lipid particles by lyophilization. Drug:lipid particles prepared according to Example 2 could be lyophilized without loss of activity. The final concentration of sucrose in which drug:lipid particles were formed was 8% (w/v). The lyophilized preparations were reconstituted by adding distilled water and their transfection activity in the lungs of mice after i.v. injection was measured. Freezing and thawing the reconstituted preparation did not affect the activity. The results shown in Table 10 demonstrate that particles prepared used the method described herein preserve their properties during lyophilization, and hence are stable. Specifically, particle size is stabilized and preserved before, during, and after lyophilization.

TABLE 10

Lyo (sucrose containing) formulations prepared using semi Single-use manufacturing train

| Batch Vol (L) | Drug Substance | drug/lipid (wt/wt) | Before Freezing | | | After Thawing | | | After Lyophilization + Reconstitution | | |
|---|---|---|---|---|---|---|---|---|---|---|---|
| | | | Size (nm) | PDI | EE (%) | Size (nm) | PDI | EE (%) | Size (nm) | PDI | EE (%) |
| 20 | siRNA 2 | 0.11 | 98 | 0.15 | 94 | 97 | 0.16 | 90 | 115 | 0.15 | 93 |

The stability of the particles is a function of the lipid composition, the lipid:RNA (w:w) values, and the choice of polysaccharide used in the formulation The methodical approach described herein for producing stable formulations of lipid:RNA complexes exhibiting high bioactivity in vivo confers advantages for establishing pharmaceutically acceptable preparations, and therefore facilitates liposome based RNA delivery.

Example 7

Submerged Injection of Lipid

The process as described in Example 3 was performed modified by preparing vesicles using submerged injection. HEDC, S104, DOPE, cholesterol, a PEG-BML, and diVA-PEG750-diVA were dissolved in ethanol at a molar ratio of 20:20:30:25:5:2. Table 11 summarizes the results of characterizing the nanoparticles resulting from the submerged addition process compared to the surface addition process. The results show the surprising and unexpected result that the mean particle size substantially decreases when the lipids are added to the aqueous phase by submerged injection.

TABLE 11

| Batch Vol [L] | Drug Substance | drug/ lipid [wt/wt] | Addition Method | Particle Size | | EE [%] | Product Yield [siRNA recovery] |
|---|---|---|---|---|---|---|---|
| | | | | Mean [nm] | PDI | | |
| Liquid Formulations prepared using semi Single-use manufacturing train | | | | | | | |
| 5 | siRNA 1 | 0.07 | Surface | 93 | 0.136 | 97 | >90% |
| 5 | siRNA 1 | 0.07 | Submerged | 57 | 0.104 | 97 | >90% |
| Frozen (sucrose containing) formulations prepared using semi Single-use manufacturing train | | | | | | | |
| 5 | siRNA 1 | 0.11 | Surface | 94 | 0.119 | 95 | >90% |
| 1 | siRNA 1 | 0.11 | Submerged | 63 | 0.102 | 95 | >90% |

The same process method was used to prepared liposomes containing sucrose in the buffer. Table 12 summarizes the results of characterizing the nanoparticles resulting from different addition times and Table 13 summarizes the results of characterizing nanoparticles prepared using surface compared to submerged addition.

TABLE 12

Liquid Formulations prepared using semi Single-use manufacturing train

| Addition Time [min] | Addition Method | Particle Size | | EE [%] | Product Yield [siRNA recovery] |
|---|---|---|---|---|---|
| | | Mean [nm] | PDI | | |
| 0.5 | Submerged | 66 | 0.140 | 90 | >90% |
| 2.0 | Submerged | 93 | 0.112 | 94 | >90% |
| 5.0 | Submerged | 99 | 0.133 | 92 | >90% |
| 10 | Submerged | 98 | 0.137 | 91 | >90% |

TABLE 13

Liquid Formulations prepared using semi Single-use manufacturing train

| Batch | | | Particle Size | | Product Yield | |
|---|---|---|---|---|---|---|
| Vol [L] | Addition Time [min] | Addition Method | Mean [nm] | PDI | EE [%] | [siRNA recovery] |
| 5 | 15 | Surface | 93 | 0.136 | 95 | >90% |
| 1 | 1.5 | Submerged | 63 | 0.102 | 95 | >90% |

The results show the surprising and unexpected result that the mean particle size substantially decreases when the lipids are added to the aqueous phase by submerged injection with an addition time of less than 2 minutes. The results also show the surprising results that mean particle size substantially decreases when the lipids are added to the aqueous phase by submerged injection.

What is claimed:

1. A system for sterilely preparing a lipid-nucleic acid nanoparticle, comprising:
   a $1^{st}$ holding unit for holding an organic lipid solution comprising lipids in a water-miscible organic solvent, wherein the $1^{st}$ holding unit comprises an inlet opening for receiving the organic lipid solution and an exit port for delivering the organic lipid solution;
   a $2^{nd}$ holding unit for holding an aqueous solution comprising an RNA molecule, wherein the $2^{nd}$ holding unit comprises an inlet opening for receiving the aqueous solution and an exit port for delivering the aqueous solution;
   a mixing unit for mixing the organic lipid solution and the aqueous solution to produce a fluid mixture, wherein the mixing unit comprises a first inlet opening for receiving the organic lipid solution by a $1^{st}$ connection from the $1^{st}$ holding unit to the mixing unit, a second inlet opening for receiving the aqueous solution by a $2^{nd}$ connection from the $2^{nd}$ holding unit to the mixing unit, and an exit port for delivering the fluid mixture;
   a $3^{rd}$ holding unit for holding an aqueous buffer, wherein the $3^{rd}$ holding unit comprises an inlet opening for receiving the aqueous buffer and an exit port for delivering the aqueous buffer;
   a dilution unit for diluting the fluid mixture with the aqueous buffer to produce a diluted fluid mixture, wherein the dilution unit comprises a $1^{st}$ inlet opening for receiving the aqueous buffer by a $3^{rd}$ connection from the $3^{rd}$ holding unit to the dilution unit, a $2^{nd}$ inlet opening for receiving the fluid mixture by a $4^{th}$ connection from the mixing unit to the dilution unit, and an exit port for delivering the diluted fluid mixture;
   a concentrating unit comprising a transflow filter for concentrating and removing the organic solvent from the diluted fluid mixture to produce a filter retentate, wherein the concentrating unit comprises an inlet opening for receiving the diluted fluid mixture by a $5^{th}$ connection from the dilution unit to the concentrating unit, and an exit port for delivering the filter retentate; and
   a vessel for collecting the filter retentate, wherein the vessel comprises an inlet opening for receiving the filter retentate by a $6^{th}$ connection from the concentration unit to the vessel and an exit port for delivery of the filter retentate;
   wherein the system consists of components that are sterilized and disposable so as to be adapted for single batch usage.

2. The system of claim 1, further comprising a preparation unit for preparing the organic lipid solution, wherein the preparation unit comprises an inlet opening for receiving an organic solvent and lipids, and an exit port for delivering the organic lipid solution by a $7^{th}$ connection from the preparation unit to the $1^{st}$ holding unit.

3. The system of claim 2, wherein the $7^{th}$ connection comprises a $6^{th}$ pump for delivering the organic lipid solution from the preparation unit to the $1^{st}$ holding unit, and $1^{st}$ 0.45 micron or 0.1 micron filter for sterilizing the organic lipid solution.

4. The system of claim 1, wherein the organic lipid solution, the aqueous solution, the fluid mixture, the diluted fluid mixture, and the filter retentate are sterile.

5. The system of claim 1, wherein
   the $1^{st}$ connection comprises a $1^{st}$ pump for delivering the organic lipid solution from the 1st holding unit to the mixing unit,
   the $2^{nd}$ connection comprises a $2^{nd}$ pump for delivering the aqueous solution from the $2^{nd}$ holding unit to the mixing unit,
   the $3^{rd}$ connection comprises a $3^{rd}$ pump for delivering the aqueous buffer from the 3rd holding unit to the dilution unit, and a $2^{nd}$ 0.45 micron or 0.1 micron filter for filtering the aqueous buffer;
   the $4^{th}$ connection comprises a $4^{th}$ pump for delivering the fluid mixture from the mixing unit to the dilution unit; and
   the $5^{th}$ connection comprises a $5^{th}$ pump for delivering the diluted fluid mixture from the dilution unit to the concentrating unit.

6. The system of claim 1, wherein the lipids comprise a cationic lipid, a helper lipid, a sterol, and a polyethylene (PEG)-lipid conjugate.

7. The system of claim 1, wherein the lipids further comprise a targeting lipid.

8. The system of claim 1, wherein the RNA is a dsRNA molecule.

9. The system of claim 1, wherein the concentration of lipid and dsRNA in the mixture consists of a RNA:lipid charge ratio of 1:2.5 to 1:1.

10. The system of claim 1, wherein the water-miscible organic solvent is ethanol.

11. The system of claim 1, wherein the $1^{st}$ holding unit and the mixing unit are thermally regulated at a temperature of 35 to 40° C.

12. The system of claim 1, wherein the aqueous solution in the $2^{nd}$ holding unit comprises a buffer at pH 3.5 to pH 6.5.

13. The system of claim 1, wherein the aqueous buffer in the $3^{rd}$ holding unit is at neutral pH.

14. The system of claim 1, further comprising
   a reservoir for mixing RNA and an aqueous buffer to produce the aqueous solution, wherein the reservoir comprises an exit port for delivering the aqueous solution by an $8^{th}$ connection from the reservoir to the $2^{nd}$ holding unit.

15. The system of claim 1, wherein the $1^{st}$ inlet opening of the mixing unit comprises a multinozzle.

16. The system of claim 15, wherein the first inlet opening is at or near the top of the mixing unit above the solution.

17. The system of claim 1, further comprising
   a collection bottle for collecting the filter retentate, wherein the collection bottle comprises an inlet opening for receiving the filter retentate by a $9^{th}$ connection from the vessel to the collection bottle, and an exit port for delivery of the filter retentate.

18. The system of claim 17, further comprising
sterile glass vials comprising an opening for receiving the filter retentate from the collection bottle.

19. The system of claim 18, further comprising a freezer unit capable of cooling the sterile glass vials at 1° C./minute to about −40° C.

20. The system of claim 19, further comprising a temperature-regulated lyophilizer unit capable of drying frozen bulk product in the glass vials, wherein the lyophilizer unit is capable of regulating a constant low temperature at about −15 to about −35° C., and a constant high temperature at about 15 to about 25° C.

21. The system of claim 14, wherein the $8^{th}$ connection comprises a $7^{th}$ pump for delivering the aqueous solution from the reservoir to the $2^{nd}$ holding unit, and a $3^{rd}$ 0.45 micron or 0.1 micron filter for filtering the aqueous solution.

22. The system of claim 17, wherein the $9^{th}$ connection comprises an $8^{th}$ pump for delivering the filter retentate from the vessel to the collection bottle, and a $4^{th}$ 0.45 micron or 0.2 micron filter for filtering the filter retentate.

* * * * *